United States Patent [19]

Cleve et al.

[11] Patent Number: 5,728,689
[45] Date of Patent: Mar. 17, 1998

[54] 11β-ARYL-4-ESTRENES, PROCESS FOR THEIR PRODUCTION AS WELL AS THEIR USE AS PHARMACEUTICAL AGENTS

[75] Inventors: Arwed Cleve; Cornelius Scheidges; Günter Neef; Eckhard Ottow; Walter Elger; Sybille Beier, all of Berlin, Germany

[73] Assignee: Schering Aktiengesellschaft, Berlin, Germany

[21] Appl. No.: 466,523

[22] Filed: Jun. 6, 1995

Related U.S. Application Data

[62] Division of Ser. No. 433,562, May 3, 1995, which is a continuation of Ser. No. 541,806, Jun. 21, 1990, abandoned.

[30] Foreign Application Priority Data

Jun. 23, 1989 [DE] Germany ............... 39 21 059.6

[51] Int. Cl.$^6$ .................. A61K 31/56; A61K 31/58
[52] U.S. Cl. ............... 514/179; 514/172; 514/174; 514/176; 514/182
[58] Field of Search ................... 514/179, 182, 514/174, 176, 172

[56] References Cited

U.S. PATENT DOCUMENTS

| | | |
|---|---|---|
| 4,386,085 | 5/1983 | Teutsch et al. . |
| 4,808,710 | 2/1989 | Jongh et al. . |
| 4,861,763 | 8/1989 | Cook et al. . |
| 4,870,069 | 9/1989 | Ottow et al. . |
| 4,900,725 | 2/1990 | Nioie et al. . |
| 4,921,846 | 5/1990 | Nedelec et al. . |
| 4,978,657 | 12/1990 | Teutsch et al. . |

FOREIGN PATENT DOCUMENTS 404283  12/1990  European Pat. Off. ......... C07J 43/00

OTHER PUBLICATIONS

Neef, et al, Tetrahedron Letters, 24(47), pp. 5205–5208 (1983).

*Primary Examiner*—Jose G. Dees
*Assistant Examiner*—Barbara Badio
*Attorney, Agent, or Firm*—Millen, White, Zelano, & Branigan, P.C.

[57] ABSTRACT

A method of inducing an antigestagenic effect by the administration of compounds of formula I:

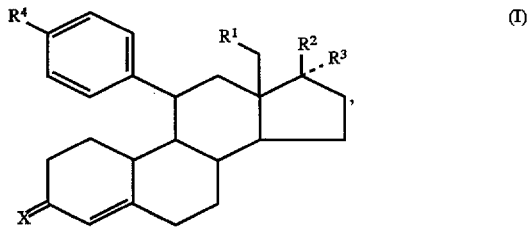

wherein, substituents are as defined in the specification.

26 Claims, No Drawings

11β-ARYL-4-ESTRENES, PROCESS FOR THEIR PRODUCTION AS WELL AS THEIR USE AS PHARMACEUTICAL AGENTS

This is a division of the application Ser. No. 08/433,562 filed 3 May 1995, which is a continuation of application Ser. No. 07/541,806 filed 21 Jun. 1990, now abandoned.

This invention relates to 11β-aryl-4-estrenes of general formula I

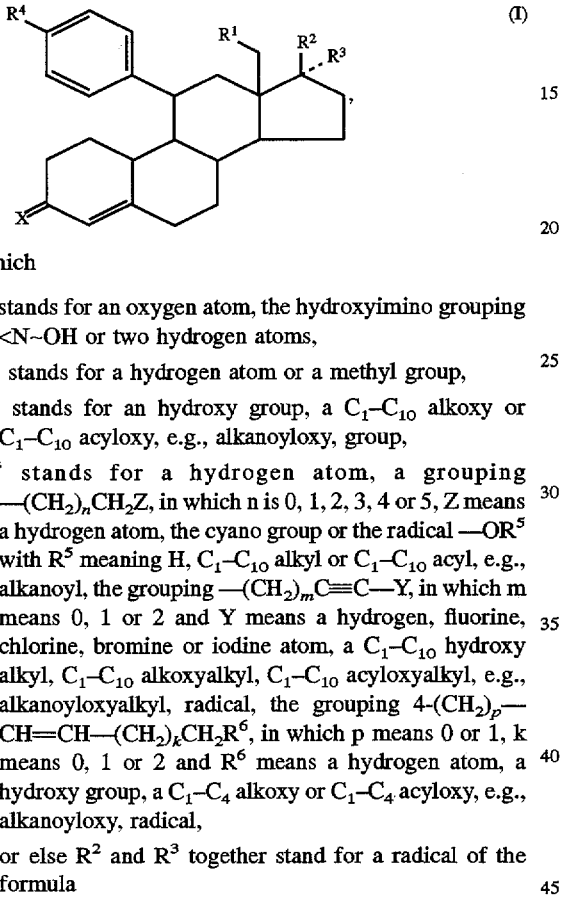

in which

X stands for an oxygen atom, the hydroxyimino grouping <N—OH or two hydrogen atoms, $R^1$ stands for a hydrogen atom or a methyl group, $R^2$ stands for an hydroxy group, a $C_1$–$C_{10}$ alkoxy or $C_1$–$C_{10}$ acyloxy, e.g., alkanoyloxy, group, $R^3$ stands for a hydrogen atom, a grouping —$(CH_2)_nCH_2Z$, in which n is 0, 1, 2, 3, 4 or 5, Z means a hydrogen atom, the cyano group or the radical —$OR^5$ with $R^5$ meaning H, $C_1$–$C_{10}$ alkyl or $C_1$–$C_{10}$ acyl, e.g., alkanoyl, the grouping —$(CH_2)_mC\equiv C$—Y, in which m means 0, 1 or 2 and Y means a hydrogen, fluorine, chlorine, bromine or iodine atom, a $C_1$–$C_{10}$ hydroxy alkyl, $C_1$–$C_{10}$ alkoxyalkyl, $C_1$–$C_{10}$ acyloxyalkyl, e.g., alkanoyloxyalkyl, radical, the grouping 4-$(CH_2)_p$—CH=CH—$(CH_2)_kCH_2R^6$, in which p means 0 or 1, k means 0, 1 or 2 and $R^6$ means a hydrogen atom, a hydroxy group, a $C_1$–$C_4$ alkoxy or $C_1$–$C_4$ acyloxy, e.g., alkanoyloxy, radical, or else $R^2$ and $R^3$ together stand for a radical of the formula

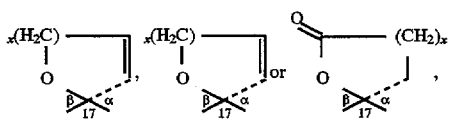

in which x=1 or 2

$R^4$ stands for a hydrogen atom, cyano, chlorine, fluorine, bromine, iodine, trialkylsilyl, trialkylstannyl, for a straight-chain or branched, saturated or unsaturated $C_{1-8}$ hydrocarbyl, $C_{1-8}$ acyl, e.g., alkanoyl, or $C_{1-8}$ alkoxyalkyl; for example, $C_{1-8}$ alkyl, $C_{3-8}$ cycloalkyl, or $C_{2-8}$ alkenyl or $C_{2-8}$ alkynyl radical, for an amino group

in which $R^7$ and $R^8$, independently of one another, mean a hydrogen atom or a $C_1$–$C_4$ alkyl group, or a corresponding amine oxide

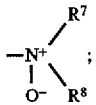

or else stands for the grouping —$OR^9$ or —$S(O)_iR^9$, wherein i means 0, 1 or 2, and in which $R^9$ means a hydrogen atom, a methyl, ethyl, propyl, isopropyl, methoxyphenyl, allyl or a 2-dimethylaminoethyl group, or for a heteroaryl radical of the formula Iα

in which A symbolizes an nitrogen, oxygen or sulfur, —B—D—E— the element sequence —C—C—C—, —N—C—C— or —C—N—C— and $R^{10}$ a hydrogen atom, a cyano, chlorine, fluorine, bromine, iodine, trialkylsilyl, trialkylstannyl or an amino group

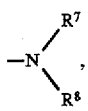

or the radical —$OR^9$ or —$S(O)_iR^9$ with $R^7$, $R^8$, $R^9$ and i each independently having one of the meanings already indicated, or for a heteroaryl radical of formula Iβ

in which A means a nitrogen atom and —B—D—E— means the element sequence —C—C—C—, —N—C—C—, —C—N—C— or —C—C—N— and $R^{10}$ has the meaning already indicated, or for a phenyl radical of formula Iτ

in which $R^{10}$ has the meaning already indicated, as well as their pharmacologically compatible addition salts with acids, processes for their production, pharmaceutical preparations containing these compounds, their use for the production of pharmaceutical agents as well as the new intermediate products necessary for this purpose.

The invention relates especially to compounds, in which X stands for an oxygen atom.

The alkoxy, acyloxy, e.g., alkanoyloxy, alkyl, acyl, e.g., alkanoyl, as well as hydroxyalkyl groups contained in $R^2$, $R^3$, $R^5$ and Y of general formula I are to contain 1 to 10 carbon atoms each and the alkoxylalkyl or acyloxyalkyl, e.g., alkanoyloxyalkyl, groups in Y contain 2 to 10 carbon atoms. In this case, the methoxy, ethoxy, propoxy and isopropoxy group can be named as preferred groups of the alkoxy groups, the formyl(oxy), acetyl(oxy) and propionyl (oxy) group from the acyl(oxy), e.g., alkanoyl(oxy), groups are especially important. In the alkyl groups above all methyl, above all ethyl, propyl, isopropyl as well as tert-butyl group can be mentioned and of the hydroxyalkyl groups the corresponding radicals substituted in any position with a hydroxy group are preferred.

0, 1, 2 and 3 are especially suitable for n; if Z=CN, a cyanomethyl group (n=0) is especially preferred. In addition the groups already mentioned, Y can preferably be a hydrogen, chlorine or bromine atom.

Of the alkenyl radicals in $R^3$, the propenyl and butenyl groups, which can be present in the E or Z configuration, are preferred, i.e., if $R^3$ stands for —$(CH_2)_p$—CH=CH—$(CH_2)_k$—$CH_2$—$R^6$, k preferably is to be 0 or 1, and p is preferably 0.

Among the alkoxy or acyloxy, e.g., alkanoyloxy, groups, which can be both straight-chain and branched, mentioned for $R^6$, methoxy, ethoxy, propoxy, isopropoxy or the formyloxy, acetyloxy and propionyloxy groups are especially preferred.

Of the $C_1$-$C_8$ alkyl and alkoxyalkyl radicals, which can stand for $R^4$, preferred are the methyl, ethyl, propyl, isopropyl, cyclopentyl and cyclohexyl radical or the alkoxy methyl and 1- or 2-alkoxyethyl groups with said alkyl radicals; of the $C_1$-$C_8$ acyl, e.g., alkanoyl, radicals for $R^4$ especially acetyl, propionyl and isobutylryl radical are preferred.

If $R^4$ stands for the amino group

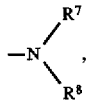

$R^7$ and $R^8$ preferably each mean a methyl radical, but the ethyl radical also has special importance, and then either both radicals on the nitrogen atom stand for an ethyl radical or one for a methyl radical and the other for an ethyl radical.

For the substituent $R^9$ the methyl, ethyl and 2-(dimethylamino)ethyl groups are especially to be emphasized.

Of the heteroaryl radicals possible according to formula Iα, the 3-thienyl, 3-furyl and 3-pyrrolyl radicals are preferred with $R^{10}$ meaning a cyano, methoxy or dimethylamino group.

As heteroaryl radicals of formula Iβ, according to the invention especially 3- or 4-pyridyl, 5-pyrimidinyl, 4-pyridazinyl or pyrazinyl radicals are suitable. The phenyl radical of formula Iτ exhibits as substituent $R^{10}$ especially the cyano, methoxy or dimethylamino group, and again these substituents preferably are in the p-position of the phenyl ring.

Compounds named below are especially preferred according to the invention:

11β-[4-(dimethylamino)phenyl]-17β-hydroxy-17α-(1-propinyl)-4-estren-3-one;
11β-(4-acetylphenyl)-17β-hydroxy-4-estren-3-one;
11β-(4-acetylphenyl)-17β-hydroxy-17α-(1-propinyl)-4-estren-3-one;
11β-(4-acetylphenyl)-17β-hydroxy-17α-(3-hydroxy-1Z-propenyl)-4-estren-3-one;
11β-[4-(dimethylamino)phenyl]-17β-hydroxy-17α-(3-hydroxy-1Z-propenyl)-4-estren-3-one;
11β-[4-(3-furyl)phenyl]-17β-hydroxy-17α-(1-propinyl)-4-estren-3-one;
11β-[4-(3-furyl)phenyl]-17β-hydroxy-17α-(3-hydroxy-1Z-propenyl)-4-estren-3-one;
11β-[4-(5-pyrimidinyl)phenyl]-17β-hydroxy-17α-(1-propinyl)-4-estren-3-one;
11β-[4-(5-pyrimidinyl)phenyl]-17β-hydroxy-17α-(3-hydroxy-1Z-propenyl)-4-estren-3-one;
11β-[4-(3-pyridyl)phenyl]-17β-hydroxy-17α-(1-propinyl)-4-estren-3-one;
11β-[4-(3-pyridyl)phenyl]-17β-hydroxy-17α(3-hydroxy-1Z-propenyl)-4-estren-3-one;
11β-[4-(4-cyanophenyl)phenyl]-17β-hydroxy-17α-(1-propinyl)-4-estren-3-one;
11β-[4-(4-cyanophenyl)phenyl]-17β-hydroxy-17α-(3-hydroxy-1Z-propenyl)-4-estren-3-one; 11β-(4-vinylphenyl)-17β-hydroxy-17α-(3-hydroxy-1Z-propenyl)-4-estren-3-one;
11β-(4-vinylphenyl)-17β-hydroxy-17α-(1-propinyl)-4-estren-3-one;
11β-[4-(1-hydroxyethyl)phenyl]-17β-hydroxy-17α-(3-hydroxy-1Z-propenyl)-4-estren-3-one;
11β-[4-(1-hydroxyethyl)phenyl]-17β-hydroxy-17α-(1-propinyl)-4-estren-3-one;
11β-[4-(dimethylamino)phenyl]-17β-hydroxy-17α-methoxymethyl-4-estren-3-one;
11β-[4-(dimethylamino)phenyl]-17β-hydroxy-17α-cyanomethyl-4-estren-3-one;
(11β,17β)-4',5'-dihydro-11-[4-(dimethylamino)phenyl]spiro[estr-4-ene-17,2'(3'H)-furan]-3-one;
(11β,17β)-3',4'-dihydro-11-[4-(dimethylamino)phenyl]spiro[estr-4-ene-17,2'(5'H)-furan]-3,5'-dione;
(11β,17β)-11-[4-(dimethylamino)phenyl]spiro[estr-4-ene-17,2'(5'H)-furan]-3-one;
11β-[4-(dimethylamino)phenyl]-17α-(1-propinyl)-4-estren-17β-ol;
17β-hydroxy-3-oxo-11β-[4-(3-pyridinyl)phenyl]-4-estren-17α-acetonitrile;
(E)-17β-hydroxy-3-(hydroxyimino)-11β-[4-(3-pyridinyl)phenyl]-4-estren-17α-acetonitrile;
(Z)-17β-hydroxy-3-(hydroxyimino)-11β-[4-(3-pyridinyl)phenyl]-4-estren-17α-acetonitrile;
17β-hydroxy-17α-(2-propenyl)-11β-[4-(3-pyridinyl)phenyl]-4-estren-3-one;
17β-hydroxy-17α-(methoxymethyl)-11β-[4-(3-pyridinyl)phenyl]-4-estren-3-one;
11β-(4-ethylphenyl)-17β-hydroxy-17α-(1-propinyl)-4-estren-3-one;
(Z)-11β-(4-ethylphenyl)-17β-hydroxy-17α-(3-hydroxy-1-propenyl)-4-estren-3-one;
(Z)-11β-[4-(2-furanyl)phenyl]-17β-hydroxy-17α-(3-hydroxy-1-propenyl)-4-estren-3-one;
11β-(4-ethylphenyl)-17β-hydroxy-17α-methyl)-4-estren-3-one;
(Z)-17β-hydroxy-17α-(3-hydroxy-1-propenyl)-11β-(4-methylphenyl)-4-estren-3-one; and
(11β,17β)-11-[4-(5-pyrimidinyl)phenyl]spiro[estr-4-en-17,2'(3'H)-furan]-3-one.

In the compounds of general formula I there are involved competitive antagonists of progesterone (antigestagens). All the steroidal antigestagens that have become known recently exhibit, besides a $\Delta^4\Delta^9$-3-oxo-chromophore, a preferably substituted 11β-phenyl radical (A. Belanger, D. Philibert and G. Teutsch, Steroids 37, 2742 (1981); D. Philibert, T. Ojasoo and J. P. Raynand, Endocrinology 10, 1850 (1977), EP-A 057 115; G. Teutsch, T. Ojasoo and J. P. Raynand, J. Steroid Biochem., 31, 549 (1988)).

Recently, antigestagens of steroidal origin have been found in which, instead of a 9,10 double bond, a methylene bridge is formed between the 9 C atom and one of the ortho C atoms of the 11β-aryl ring (EP-A 0283428). Obviously an introduction of the 11β-aryl radical causes the transition from gestagen to antigestagen action. However, so far it has not been possible to produce an antigestagen coming closest to progesterone, so to speak "the antiprogesterone," which would exhibit no 9,10 double bond but, besides an 11β-aryl radical a "free" 10β-substituent, e.g., a hydrogen atom. Attempts to isomerize 11β-[4-(substituent)-aryl]-17β-hydroxy-5(10)-estren-3-one by short-term treatment with dilute mineral acids into the corresponding compound with a 4(5) double bond, conditions, under which in the 11-unsubstituted series a double bond shift from the 5(10) into the 4(5) position easily takes place, failed (G. Neef, G. Sauer and R. Wiechert, Tet. Let., 24, 5205 (1983)).

But now conditions have been found, under which in a surprising way it is possible to bring about a shift of the 5(10) double bond into the 4(5) position.

Treatment of the compounds of general formula II

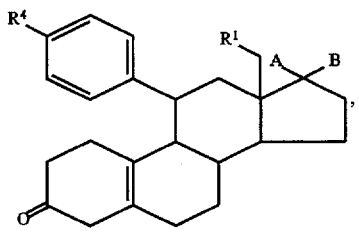

(II)

in which

R¹ and R⁴ have the meaning indicated in formula I,

A stands for a β-hydroxy group or the radical R² and

B stands for an α-hydrogen atom, an α-position radical R³ or

A and B together stand for a keto oxygen atom, with acid in an inert solvent with heating leads to compounds of general formula Ia

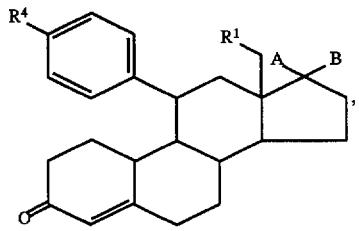

(Ia)

in which R¹, A and B have the meaning indicated in formula II and R⁴' has the same meaning as R⁴ in formula I, provided that R⁴ is stable under said drastic reaction conditions.

Preferably for the isomerization, the reaction is conducted at temperatures between 60° and 120° C., most preferably between 60°–90° C. Suitable inert solvents for the reaction are various hydrocarbon solvents, such as, for example, toluene, benzene, and various chlorinated hydrocarbon solvents, such as, for example, CHCl₃. Toluene is preferred.

The reaction time is at least 45 minutes, but, if necessary, can be 24 hours or more. The preferred reaction time is 3–4 hours.

As acids both mineral acids, e.g., HCl, and organic acids, e.g., p-toluenesulfonic acid, benzenesulfonic acid and trifluoroacetic acid, are suitable. Of the latter, p-toluenesulfonic acid is preferred. The acids will generally have a minimum $pK_a$ of from +1 to −7.

In general, the reaction will be carried out under non-aqueous conditions, with concentrations of the starting steroid in the range of 0.05 to 0.10 mol.

With the compounds of general formula Ia, an end compound of general formula I can already be involved, if the substituents R⁴, A and B in the starting compound of general formula II are such substituents that withstand the drastic reaction conditions necessary for the isomerization. Especially free hydroxy groups on a tertiary carbon atom are eliminated under these reaction conditions.

But in any case it can be wise first, after the isomerization, to introduce the substituents R² and R³ on the C 17 atom or add R⁴ in the 4 position of the 11β-phenyl radical. Depending on the substituents R², R³ and R⁴ finally desired in the compound of general formula I, after the isomerization, optionally either a) in the compound of general formula Ia, if in it A stands for a β-hydroxy group and B for an α-hydrogen atom, optionally the 17-hydroxy group is oxidized to the 17-keto group and b) the 3-keto function is converted into a dithioketal, and all other optionally present keto groups are also ketalized or else first b) and then a) are performed and then c) in the case that R⁴ in the 3-thioketalized compound stands for a methoxy or a hydroxy group and R⁴ in the finally desired compound of general formula I is not to stand for a methoxy or hydroxy group, the hydroxy compound, optionally after cleavage of the methoxy compound, is converted into a corresponding perfluoroalkyl sulfonic acid compound, in which -alkyl- stands for a $C_1$–$C_4$ alkyl radical, and from the latter either directly by reaction with a corresponding substituted tin(trialkyl) compound R⁴" Sn(alkyl)₃ or with a corresponding substituted boron compound R⁴"-BL₂(L=hydroxy or alkyl), in which R⁴" is identical with R⁴ of general formula I or represents a tautomer precursor of R⁴ and -alkyl- means a $C_1$–$C_4$ alkyl radical, or indirectly by a compound substituted in the 4 position of the 11β-phenyl radical with a tin(trialkyl) radical (alkyl=$C_1$–$C_4$), which was obtained by reaction of the perfluoroalkyl sulfonate compound with Sn₂alkyl₆, and further treatment of the 11β-(4-trialkylstannyl)-phenyl compound with a compound R⁴"-Y, in which R⁴" is identical with R⁴ of general formula I or represents a tautomer precursor of R⁴ and Y means a starting group, preferably a halogen atom and especially a bromine atom, in the presence of a transition metal catalyst, a compound of general formula III

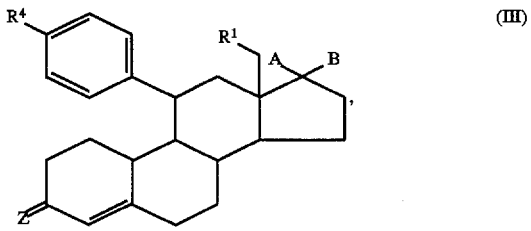

(III)

in which Z means keto group protected in the form of a dithioketal, is produced, and d) then, if R² and R³ in the finally desired compound of general formula I are not to stand for a hydroxy group or a hydrogen atom or else R² and R³ together are not to stand for a keto oxygen atom, the desired substituents R² and R³ are introduced on the C 17 atom of the steroid skeleton according to methods known in the art or else first d) and then c) can be performed, protecting groups are cleaved, optionally free hydroxy groups are alkylated or acylated and optionally with hydroxylaminohydrochloride the 3-keto group is converted into a 3-hydroxyimino grouping >N—OH or the 3-keto group into the dihydro compound as well as optionally a pharmaceutically compatible addition salt is produced with an acid.

The performance of process steps a), b), c) and d) takes place according to methods known in the art.

Oxidation a) of the hydroxy group to the keto group can be performed, for example, according to Oppenauer or with chromic acid reagents (Jones reagent) or chromic acid pyridine.

As protecting group for the 3-keto function the ethane-1, 2-diyl-bis(thio) group is preferably used, which by reaction of the 3-keto compound with ethane-1,2-dithiol in the presence of, e.g., p-toluenesulfonic acid can be introduced on the steroid 3 C atom.

Alternately first the oxidation and then the protecting group introduction or first the protecting group introduction and then the oxidation are performed.

Reaction step c) serves to add substituents R4 or $R^{4'}$ in the p-position on the 11β-phenyl ring. This way of proceeding is necessary, if $R^4$ represents a substituent, which does not withstand the drastic isomerization conditions, for example, an allyl or vinyl radical.

As starting material for this addition, the 11β-(4-hydroxyphenyl) compound is used, which can be obtained from the corresponding methoxy compound by ether cleavage, for example, with sodium methane thiolate in a solvent such as dimethylformamide.

By reaction of the hydroxy compound with a perfluoro-$(C_1-C_4)$-alkyl sulfonic acid anhydride or halide in the presence of a base such as pyridine or 4-(dimethylamino) pyridine, the corresponding 11β-[4-(perfluoroalkyl sulfonyloxy)-phenyl] compound is obtained (P. J. Stang, M. Hanack and L. R. Subramanian, Synthesis 85, (1982)).

For the coupling of the 11β-aryl compound with either the $R^{4''}$-Sn(alkyl)$_3$ or the $R^{4''}$-BL$_2$ groups, the procedure is such that either in a reaction catalyzed by a transition metal (preferably Pd°), the perfluoroalkyl sulfonate starting group with basically almost simultaneous substitution is displaced by the desired substituent or its precursor (aryl coupling with tin compounds: J. E. McMurry and S. Mohanraj, Tetrahedron Letters, 24, No. 27, pp. 2723–2726, 1983; X. Lu and J. Zhu, Communications, pp. 726–727, 1987; Q.-Y. Chen and Z.-Y. Yang, Tetrahedron Letters 27, No. 10, pp. 1171–1174, 1986; S. Cacchi, P. G. Ciattini, E. Morera and G. Ortar, Tetrahedron Letters, 27, No. 33, pp. 3931–3934, 1986; E. M. Echavarren and J. K. Stille, J. Am. Chem. Soc. 1987, 109, pp. 5478–5486; aryl coupling with boron compounds: Synthesis 936 (1984); Chem. Pharm. Bull. 33, 4755–4763 (1985); J. Org. Chem. 49, 5237–5243 (1984); Bull. Chem. Soc. Jpn. 61, 3008–3010 (1988)) or a corresponding triorganylstannyl, preferably tri-n-alkylstannyl compound, intermediately and catalyzed by a transition metal, is produced from the perfluoroalkyl sulfonate compound [J. K. Stille, Angew. Chem. 98 (1986), pp. 504–519]. It is then reacted in a one-pot reaction with a halogen, preferably, bromine and iodine substituted carbocyclic or heterocyclic aromatic substance [Y. Yamamoto, Y. Azuma, H. Mitoh, Communications, pp. 564–565, 1986; T. J. Bailey, Tetrahedron Letters, 27, No. 37, pp. 4407–4410, 1986], which optionally can also carry other substituents; the 11β-phenyl radical then exhibits in it the desired or a precursor of the desired substitution.

Numerous such reactions with steroids, in which a trifluoromethane sulfonate group is found in the 4 position of an 11β-phenyl ring, are described in EP-A-0283428.

Free hydroxy groups can be alkylated or acylated in a way known in the art.

Dialkylamines can be converted by suitable oxidizing agents (e.g., hydrogen peroxide or peracids) into the desired N oxides [see, e.g., Kontakte (Darmstadt), 1986, 3, p. 12].

Compounds with a dialkylamine substituent on the 11β-phenyl ring by reaction with cyanogen bromide in aprotic solvents such as, for example, dioxane, benzene or toluene at elevated temperature (amine decomposition according to Braun) analogously to instructions indicated for the example in Org. Reactions 7, 198 (1935), K. W. Bentley, Techniques of Organic Chemistry 11, 773 (1963) and Houben-Weyl, 5/4, 151 (1960) can be corrected in good yield into the corresponding (N-cyano-N-alkylaminoaryl) derivatives.

Depending on the finally desired meaning of

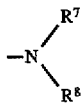

in the end product these derivatives in a way known in the art are reduced to the corresponding dialkylamine compounds (for example, with diisobutylaluminium hydride in toluene to the N-formyl-N-alkylaminophenyl intermediate products and then with lithium aluminum hydride) or N—H—N alkyl compounds (for example, with lithium aluminum hydride or with lithium in liquid ammonia). The latter are then optionally acylated in a way known in the literature and optionally then are reduced in a known way, e.g. with lithium aluminum hydride to the new dialkylamine derivative (see DE 36 23 038).

Finally, in process step d) the substituents $R^2$ and $R^3$, finally desired on the 17 C atom, are introduced, if in this case there are not involved a methoxy or hydroxy group already contained as $R^2$ from the beginning or a hydrogen atom as $R^3$ or a keto oxygen atom formed jointly from $R^2$ and $R^3$. This introduction takes place analogously to processes known in the literature (for example, J. Fried, J. A. Edwards, "Organic Reactions in Steroid Chemistry," Van Nostrand Reinhold Company, 1972, Vol. 1 and 2; "Terpenoids and Steroids," Specialist Periodical Report, The Chemical Society, London, Vol. 1–2) by nucleophilic addition on the C 17 ketone.

The introduction of the substituent —C≡C—Y as $R^3$, in which Y has the meaning indicated above, takes place with the help of a metallized compound of general formula MC≡C—Y', in which Y' is an alkine protecting group, such as, for example, trimethylsilyl or tert-butyldimethylsilyl.

The organometallic compound can also be formed in situ and reacted with the 17 ketone. Thus, for example, it is possible to cause acetylene and an alkali metal, especially potassium, sodium or lithium, in the presence of an alcohol or in the presence of ammonia, to act on the 17 ketone in a suitable solvent. The alkali metal can also be effective in the form, for example, of methyllithium or butyllithium. Especially dialkyl ether, tetrahydrofuran, dioxane, benzene and toluene are suitable as solvents.

The introduction of 3-hydroxypropine, hydroxypropene or hydroxypropane in the 17 position takes place by reaction of the 17-ketone with the dianion of propargyl alcohol (3-hydroxypropine), for example, with the dipotassium salt of the propargyl alcohol, generated in situ, to the 17α-(3-hydroxyprop-1-inyl)-17β-hydroxy derivative or with metallized derivatives of the 3-hydroxypropine, for example, with 1-lithium-3-(tetrahydropyran-2'-yloxy)-prop-1-in-1-ide, to the 17-[3-(tetrahydropyran-2'-yloxy)-prop-1-inyl]-17β- hydroxy derivative, which then can be hydrogenated to the 17-(3-hydroxypropyl or hydroxypropenyl)-17β-hydroxy compounds. This comes about, for example, by hydrogenation at room temperature and normal pressure in solvents such as methanol, ethanol, propanol, tetrahydrofuran (THF) or ethyl acetate with addition of noble metal catalysts such as platinum or palladium.

The introduction of homologous hydroxyalkine, hydroxyalkene and hydroxyalkane groups takes place in a corresponding way with homologs of the propargyl alcohol.

The compounds with the Z-configured double bond in the hydroxypropenyl group results by hydrogenation of the acetylene triple bond with a deactivated noble metal catalyst (J. Fried, J. A. Edwards: Organic Reactions in Steroid Chemistry. Van Nostrand Reinhold Company 1972, page 134; and H. O. House: Modern Synthetic Reactions 1972, p. 19). Suitable as deactivated noble metal catalysts are, for example, 10% palladium on barium sulfate in the presence of an amine or 5% palladium on calcium carbonate with addition of lead(II) acetate. The hydrogenation is interrupted after the absorption of an equivalent of hydrogen.

The compound with the E-configured double bond in the hydroxypropenyl group results by reduction of the acetylene triple bond in a way known in the art. In the literature a whole series of methods are described for the conversion of alkines into transolefins, for example, the reduction with sodium in liquid ammonia (J. Am. Chem. Soc. 63 (1941) 216) with sodium amide in liquid ammonia (J. Chem. Soc. 1955, 3558), with lithium in low-molecular amines (J. A. Chem. Soc. 77 (1955) 3378) with boranes (J. Am. Chem. Soc. 93 (1971) 3395 and 94 (1972) 6560), with diisobutylaluminum hydride and methyllithium (J. Am. Chem. Soc. 89 (1967) 5085) and especially with lithium aluminum hydride/alcoholate (J. Am. Chem. Soc. 89 (1967) 4245). Another possibility is the reduction of the triple bond with chromium(II) sulfate in the presence of water or dimethylformamide in weakly acidic medium (J. Amer. Chem. Soc. 86 (1964) 4358) as well as generally the reduction by the action of transition metal compounds with changing of the oxidation step.

The introduction of the hydroxyalkenes can also take place directly by addition of a corresponding metallized hydroxyalkenyl compound, such as, for example, 1-lithium-3-(tetrahydropyran-2'-yloxy)-prop-1(E)-ene (J. Org. Chem.40 2265) or 1-lithium-3-(tetrahydropyran-2'-yloxy)-prop-1(Z)-ene (Synthesis 1981, 999). Homologs can also be introduced in this way.

The introduction of 3-hydroxypropane in the 17 position can also take place by direct reaction of the 17-ketone with metallized derivatives of 3-halopropanols—and the hydroxy group in the metallizing step is present as alcoholate (Tetrahedron Letters 1978, 3013) or as protected function (J. Org. Chem. 37, 1947)—to the 17-(3-hydroxypropyl)- 17β-hydroxy compound or to the compound protected on the terminal hydroxy group. Ethoxyethyl, tetrahydropyranyl and methoxymethyl groups are suitable, for example, as protecting groups.

If end products of formula I are desired with R²/R³ meaning

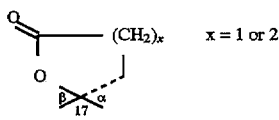

thus the 17-(3-hydroxypropyl) or 17-(4-hydroxybutyl) compound is oxidized in a way known in the art, for example with Jones reagent, manganese oxide, pyridinium dichromate, pyridinium chlorochromate, chromic acid pyridine or the Fetizon reagent silver carbonate/Celite (Comp. rend. 267 [1968] 900).

The preparation of end products of formula I with R²/R³ meaning

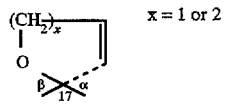

takes place by cyclization reaction of the corresponding 17-(3-hydroxyprop-1-(Z)-enyl or 17-(4-hydroxybut-1-(Z)-enyl-17β-hydroxy educt. Hydrogenation of the unsaturated 5- or 6-ring spiroether on palladium/activated carbon leads to the saturated spiroether.

The synthesis of the 17-cyanomethyl side chain takes place in a way known in the art from the 17-ketone, for example, by the 17-spiroepoxide and cleavage of the spiroepoxide with HCN according to Z. Chem. 18 (1978) 259–260.

Also the introduction of the 17-hydroxyacetyl side chain takes place according to methods known in the art described, for example, according to J. Org. Chem. 47 (1982), 2993–2995, Chem. Ber. 113 (1984), 1184 or U.S. Pat. No. 4,600,538.

Free hydroxy groups can be alkylated or acylated in a way known in the art.

Optionally also the introduction of substituents R² and R³, as described under d), can first be performed and then according to c) substituent R⁴ is added depending on whether the process conditions of the second reaction step adversely affect the first introduced but added substituents.

Still present protecting groups are cleaved according to usual methods.

The resulting compounds of general formula I with X meaning an oxygen atom, optionally by reaction with hydroxylamino hydrochloride in the presence of tertiary amines at temperatures between −20° and +40° C., can be converted into the oximes (formula I with X meaning the hydroxyimino grouping >N~OH, and the hydroxy group can be in syn- or anti-position). Suitable tertiary bases, for example, are trimethylamine, triethylamine, pyridine, N,N-dimethylaminopyridine, 1,5-diazabicyclo[4.3.0]non-5-ene (DBN) and 1,8-diazabicyclo[5.4.0]undec-7-ene (DBU), and pyridine is preferred.

Removal of the 3-oxo group for an end product of general formula I with X meaning 2 hydrogen atoms can take place, e.g., according to the instructions indicated in DE-A-2805490 by reductive cleavage of the thioketal.

The new compounds of general formula I as well as their addition salts with pharmaceutically compatible acids are valuable pharmaceutical agents for use in mammals, including humans. Thus they have a strong affinity for the gestagen receptor and have surprisingly strong antigestagen as well as antiglucocorticoid, antimineralocorticoid and antiandrogen properties. These important biological availabilities can be used for medicinal proposes.

Active ingredients of this type with marked antigestagen activity are suitable for inducing abortions, since they displace progesterone from the receptor necessary for maintaining the pregnancy. They therefore are valuable and advantageous in regard to their use for postcoital fertility control. Moreover, the new compounds can be used for treatment of endometriosis. They can also be used against hormonal irregularities, for inducing menstruation and for inducing labor. Further, they can be used for treatment of hormone-dependent carcinomas. For antigestagenic uses, the compounds of this invention can be used analogously to the known agent, RU-486.

The compounds according to the invention of general formula I as well as their addition salts with pharmaceutically compatible acids also exhibit an antiglucocorticoid activity and thus can be used also as pharmaceutical agents for therapy of corticoid-induced diseases (glaucoma) as well as for combatting of side effects, which occur in the long-term treatment with glucocorticoids (Cushing's syndrome). Therefore they make it possible to combat diseases attributable to hypersecretion of glucocorticoids, especially adiposity, arteriosclerosis, hypertension, osteoporosis, diabetes as well as insomnia. For antiglucocorticoid uses, the compounds of this invention can also be used analogously to the known agent, RU-486.

The compounds according to the invention of general formula I as well as their addition salts with pharmaceutically acceptable acids with antimineralocorticoid activity can be used in the treatment of diseases in which mineralocorticoid effects are involved, e.g., high blood pressure caused by hyperaldosteronism. Antimineralocorticoid activity of the compounds of this invention can be determined routinely, e.g., according to the methods of G. Hollmann et al., "Tubulaere Wirkungen und renale Elimination von Spirolactonen: (Tubular Effects and Renal Elimination of Spirolactones), Naunyn-Schmiedebergs Arch. Exp. Path. Pharmak. 247, 419 (1964) and P. Marx, "Renal Effects of d-Aldosterone and Its Antagonist Spironolactone", dissertation of the Medical Faculty, Berlin Free University, 1966.

The compounds according to the invention of general formula I as well as their addition salts with pharmaceutically compatible acids with antiandrogen activity can be used in the treatment of hypertrophy and prostate carcinoma. Further, they make possible a specific therapy of androgenizing phenomena in women: pathological hair in hirsutism, androgenic alopecia as well as increased sebaceous gland function in the case of acne and seborrhea can be favorably influenced. Antiandrogenic activity of the compounds of this invention can be routinely determined, e.g., according to the methods of Methods in Hormone Research, R. I. Dorfman, ed., Academic Press, New York, London, (1969), p. 241, and Androgens and Antiandrogens, L. Martini and M. Motta, eds., Raven Press, New York, (1977), p. 163.

The invention thus relates also to pharmaceutical agents on the basis of the compounds of general formula I as well as their addition salts with pharmaceutically compatible acids, optionally together with the usual auxiliary agents and vehicles.

The compounds according to the invention and their salts can be processed according to methods of galenicals known in the art into pharmaceutical preparations for enteral, percutaneous, parenteral or local application. They can be administered in the form of tablets, dragees, gelatin capsules, granules, suppositories, implants, injectable sterile aqueous or oily solutions, suspensions or emulsions, ointments, creams and gels.

The active ingredient or ingredients in this case can be mixed with the auxiliary agents usual in galenicals such as, for example, gum arabic, talc, starch, mannitol, methylcellulose, lactose, surfactants such as Tween® or Myrj®, magnesium stearate, aqueous or nonaqueous vehicles, paraffin derivatives, wetting, dispersing, emulsifying agents, preservatives and aromatic substances for taste correction (e.g., essential oils).

The invention thus relates also to pharmaceutical compositions, which contain as active ingredient at least one compound according to the invention or one of its addition salts with pharmaceutically compatible acids. As addition salts of the products according to the invention with acids hydrochlorides and methane sulfonates can be especially mentioned.

A dosage unit contains about 1–100 mg of active ingredient(s).

The dosage of the compounds according to the invention is about 1–1000 mg per day in a human. Preferred dosage ranges can be routinely determined for the various compounds, for the treatment of various conditions, depending upon the metabolism of the patient, route of administration, etc. Preferred dosage range for antigestagenic uses is about 25–500 mg/day; for antiglucocorticoid uses the preferred dosage range is about 50–1000 mg/day.

The abortive effect was determined for the characterization of the antigestagen effect.

The tests were conducted on female rats weighing about 200 g. After pairing was completed, the beginning of pregnancy was secured by detection of spermatozoa in vaginal smears. The day of determination of the spermatozoa is taken as day 1 of the pregnancy (=d1 p.c.).

The treatment of the animals with the substance or solvent to be tested in each case took place after nidation of the blastocysts from d5 p.c. to d7 p.c. On d9 p.c. the animals were killed and the uteri were examined for implants and resorption sites. Photographs were taken of all the uteri. The lack of implants, pathological, hemorrhagic or otherwise abnormal nidation sites was judged as abortion.

The test substances was dissolved in a benzylbenzoate castor oil mixture (ratio 1+4). The vehicle volume per individual dose was 0.2 mL. The treatment took place subcutaneously.

The superiority of the compounds according to the invention is unambiguously verified by comparison of the abortive effectiveness of compounds A to E with compound F described in European specification 0057 115; comparison compound F (=RU 486) differs from compound A only by the additional 9(10) double bond. As antigestagens there were examined:

A: 11β-[4-(dimethylamino)phenyl]-17β-hydroxy-17α-(1-propinyl)-4-estren-3-one

B: (Z)-11β-[4-(dimethylamino)phenyl]-17β-hydroxy-17α-(3-hydroxy-1-propenyl)-4-estren-3-one C: (Z)-11β-(4-acetylphenyl)-17β-hydroxy-17-α-(3-hydroxy-1-propenyl)-4-estren-3-one D: (Z)-17β-hydroxy-17α-(3-hydroxy-1-propenyl)-11β-[4-(3-pyridinyl)phenyl]-4-estren-3-one E: (Z)-4'-[17β-hydroxy-17α-(3-hydroxy-1-propenyl)-3-oxo-4-estren-11β-yl]-[1,1'-biphenyl]-4-carbonitrile F: 11β-[4-(dimethylamino)phenyl]-17β-hydroxy-17α-(1-propinyl)-4,9(10)estradien-3-one Abortive test in pregnant rats . . . Treatment from d5 p.c. to d7 p.c.; autopsy on d9 p.c.

| Compound | Dose mg/animal/day s.c. | Abortion Rate n abortion/n total | % |
|---|---|---|---|
| A | 3.0 | 4/4 | (100) |
|  | 1.0 | 4/4 | (100) |
|  | 0.3 | 3/4 | (75) |
| B | 3.0 | 4/4 | (100) |
|  | 1.0 | 4/4 | (100) |

-continued

| Compound | Dose mg/animal/day s.c. | Abortion Rate n abortion/n total | % |
|---|---|---|---|
|  | 0.3 | 4/4 | (100) |
| C | 3.0 | 4/4 | (100) |
|  | 1.0 | 4/4 | (100) |
|  | 0.3 | 4/4 | (100) |
|  | 0.1 | 4/4 | (100) |
| D | 3.0 | 4/4 | (100) |
|  | 1.0 | 4/4 | (100) |
|  | 0.3 | 4/4 | (100) |
| E | 3.0 | 4/4 | (100) |
|  | 1.0 | 4/4 | (100) |
|  | 0.3 | 4/4 | (100) |
|  | 0.1 | 4/4 | (100) |
| F | 3.0 | 4/4 | (100) |
|  | 1.0 | 2/4 | (50) |
|  | 0.3 | 0/4 | (0) |
| Solvent as control: 0.2 ml of benzyl- benzoate/castor oil (1:4) | — | 0/5 | (0) | n = 4 rats

Production of the necessary intermediate products of general formula II

The production of starting compound A, 3,3-[2,2-dimethyl-1,3-propanediylbis(oxy)]-5α,10α-epoxy-estr-9(11)-en-17β-ol, necessary for all syntheses, is described in EP-A-0110434 or EP-A-0127864.

For $R^4$=—$N(CH_3)_2$ the preparation of 11β-[4-(dimethylamino)phenyl]-17β-hydroxy-17α-(1-propinyl)-5(10)-estren-3-one (1M) is indicated as representative of a compound of general formula II.

By use of another nucleophilic reagent such as propine in synthesis step 1L, under conditions as indicated above in the description, the other radicals $R^2/R^3$, provided according to the invention, can be introduced.

The production of 3,3-(2,2-dimethyl-1,3-propanediylbis(oxy)]10β,11β-(5-methoxy-o-phenylenethio)-estran-5α,11β-diol is shown in example 2.

As described in example 1, optionally with the use of another nucleophilic reagent such as propine in the analogous performance of step 1L, compounds of general formula II are achieved, in which $R^{4'}$ stands for a methoxy group.

Additional starting products of general formula II can be produced as shown in the following reaction scheme (the meanings of substituents $R^1$, $R^2$, $R^3$, $R^{4'}$ and $R^4$ are identical with those of the general formulas):

In the case of compounds D, E and L, compounds of general formula II are involved.

Reaction steps F→I are performed with those compounds F in which $R^{4'}$ stands for a hydroxy group. The latter optionally is introduced by cleavage of the corresponding methyl ether.

Steps F→I as well as I→K are performed analogously to triflate formation performed and described after isomerization with subsequent coupling in the 4 position of the 11β-aryl radical.

[Key to reaction scheme]

Deketalisierung in 3 stellung Deketalization in the 3 position Oxidation von Oxidation of Ketalisierung Ketalatization Aufbau der . . . Seitenketten Addition of the . . . side chains Triflatbildung Triflate formation Wenn If D, E und L sind . . . D, E and L are compounds of general formula II

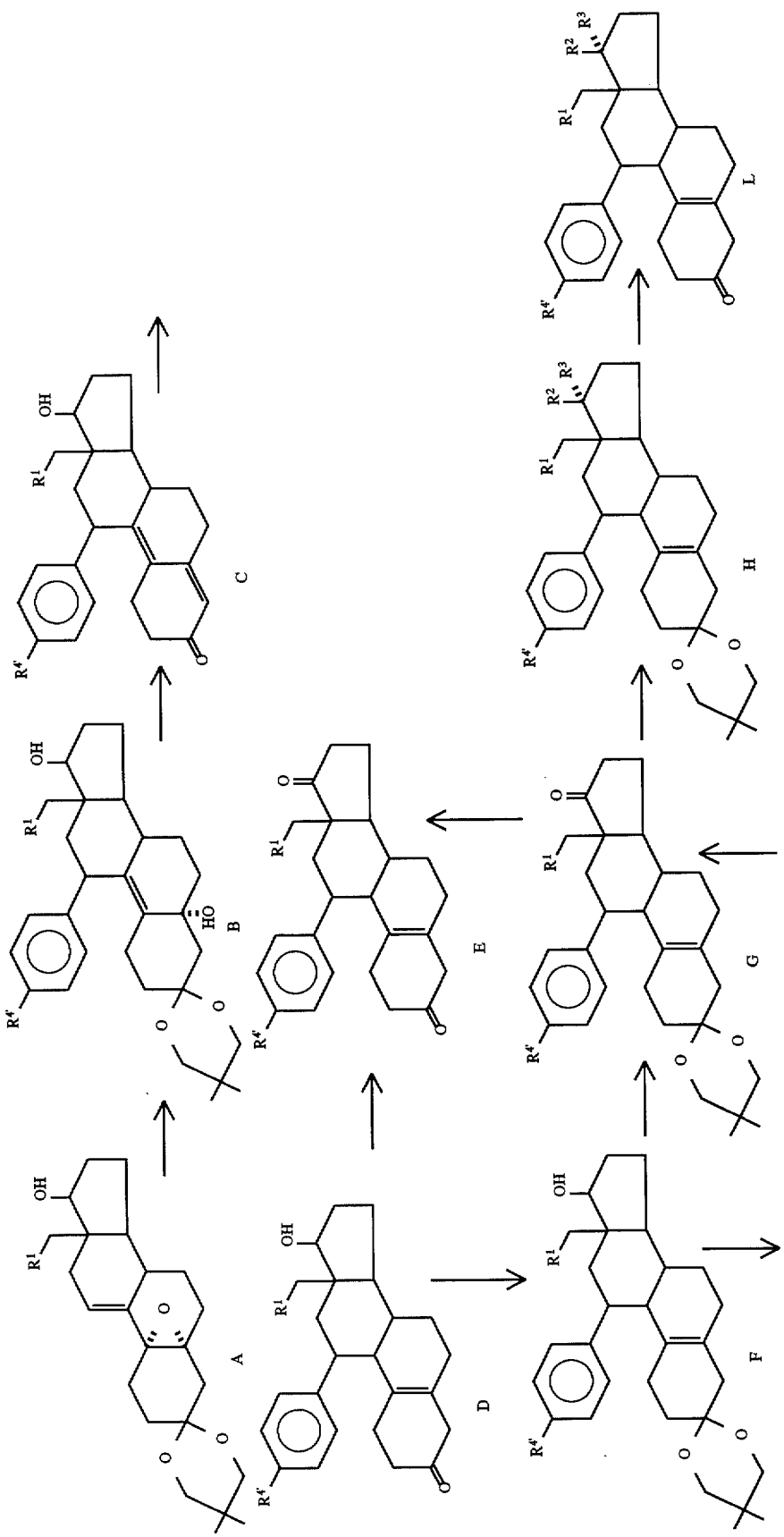

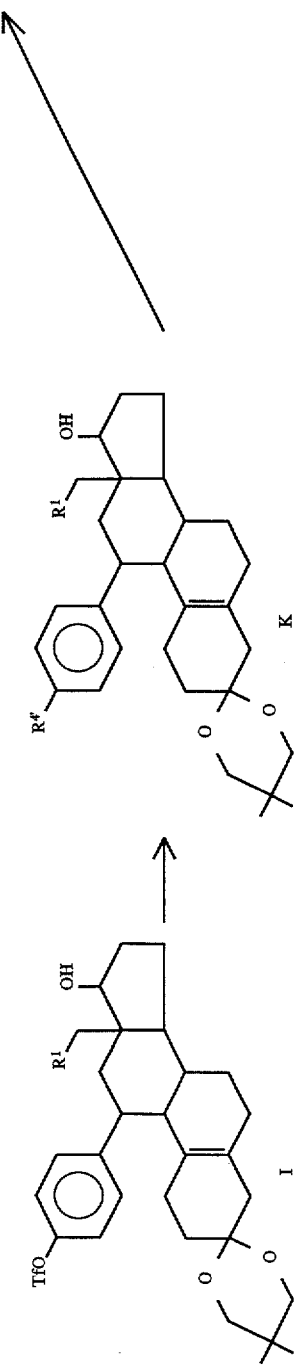

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of West German corresponding applications(s) P 39 21 059.6, are hereby incorporated by reference.

The column chromatographic purification steps in the following examples, unless otherwise indicated, are performed on silica gel with hexane/ethyl acetate, optionally with a mixture of increasing polarity.

EXAMPLES

Example 1

Preparation of 11β-[4-(Dimethylamino)phenyl]-17β-hydroxy-17α-(1-propinyl)-4-estren-3-one (1N)

A. 10β-[(3-Aminophenyl)thio]-3,3-[2,2-dimethyl-1,3-propanediylbis(oxy)]-9(11)-estrene-5α,17β-diol (1A)

750 mg of 3-mercaptoaniline is dissolved in 5 ml of absolute THF and mixed at −40° C. with 3.73 ml of a 1.6 molar n-butyllithium solution in hexane. The cooling is removed and it is stirred for 30 minutes. Now 500 mg of 3,3-[2,2-dimethyl-1,3-propanediylbis(oxy)]-5α,10α-epoxy-estr-9(11)-en-17β-ol, dissolved in 4 ml of absolute THF, is instilled, and the temperature is kept at 0° C. Then it is stirred for two more hours at room temperature. The reaction mixture is mixed with 15 ml of saturated NH$_4$Cl solution and extracted with ethyl acetate, the organic phase is washed with water and dried on Na$_2$SO$_4$, the solvent is removed in a vacuum. Column chromatography yields 484 mg of 1A as foam.

B. 3,3-[2,2-Dimethyl-1,3-propanediylbis(oxy)]-10β-[(3-(formylamino)phenyl]thio)-9(11)-estr-ene-5α,17β-diol (1B)

0.4 ml of acetic anhydride and 0.17 ml of formic acid are combined and stirred at room temperature for 15 minutes under argon. 1.0 g of 1A, dissolved in 5 ml of reagent-grade pyridine, is added to this solution and stirred at room temperature under argon for 2 more hours.

Then the reaction mixture is taken up in ethyl acetate, shaken with saturated NaHCO$_3$ until a pH of about 8 is reached, washed with water, dried on Na$_2$SO$_4$ and concentrated by evaporation in the rotary evaporator.

Yield according to column chromatography: 935 mg of 1B, foam.

C. 3,3-[2,2-Dimethyl-1,3-propanediylbis(oxy)]-10β-[(3-(methylamino)phenyl]thio]-9(11)-estr-ene-5α,17β-diol (1C)

9.4 g of 1B and 2.5 g of lithium aluminum hydride are refluxed in 400 ml of absolute THF at 80° C. under argon for 1 hour.

Then the excess lithium aluminum hydride is hydrolyzed with water, diluted with ethyl acetate, the organic phase is separated and washed with water, dried on Na$_2$SO$_4$ and the solvent is removed on the rotary evaporator.

Yield according to column chromatography: 8.4 g of 1C, foam.

D. 3,3-[2,2-Dimethyl-1,3-propanediylbis(oxy)]-10β-[3-(N-formyl-N-methylamino)-phenyl]thio]-9(11)-estr-ene-5α,17β-diol (1D)

Performance and working up as in example 1B.

Amounts used: 8.6 g of 1C, 3.39 ml acetic anhydride, 1.4 ml of formic acid, 45 ml of reagent-grade pyridine.

Yield according to column chromatography: 6.0 g of 1D, foam.

E. 10β-[3-Dimethylamino)-phenyl]thio]-3,3-[2,2-dimethyl-1,3-propanediylbis(oxy)]-9(11)-estr-ene-5α,17β-diol (1E)

3.95 g of 1D is dissolved in 150 ml of abs. THF and mixed at 0° C. under argon with 1.46 ml of a 10 molar borane dimethyl sulfide complex solution in THF. It is stirred for 2.5 more hours at room temperature. The reaction mixture is slowly mixed with 4 ml of methanol at 0° C. and allowed to stand overnight. Then it is diluted with H$_2$O and ethyl acetate. The organic phase is separated, washed with H$_2$O, dried on Na$_2$SO$_4$ and concentrated by evaporation in a vacuum. Yield according to column chromatography: 3.6 g of 1E, foam.

F. 10β-[[2-Bromo-5-dimethylamino)-phenyl]thio]-3,3-[2,2-dimethyl-1,3-propanediylbis(oxy)]9(11)-estr-ene-5α, 17β-diol (1F)

5 g of 1E is dissolved in 200 ml of CCl$_4$, is mixed with 1.65 g of N-bromosuccinimide at 0° C. and stirred for 2 hours under argon at 0° C. The reaction mixture is diluted with CH$_2$Cl$_2$ and mixed with saturated NaHCO$_3$ solution, the organic phase is washed with water and dried on Na$_2$SO$_4$ and the solvent is removed on the rotary evaporator.

Yield according to column chromatography: 2.7 g of 1F foam.

G. 10β,11β-[5-(Dimethylamino)-o-phenylenethio]-3,3-[2,2-dimethyl-1,3-propanediylbis(oxy)estrane-5α,17β-diol (1G)

1.7 g of 1F, 1.15 ml tri-n-butyltin hydride and 30 mg of azobisisobutyronitrile are stirred in 115 ml of reagent-grade toluene under argon and reflux for one hour in the light of a 300-W incandescent bulb.

Column chromatography yields 675 mg of 1G as foam.

H. 11β-[4-(dimethylamino)-2-(methylthio)-phenyl]-3,3-[2,2-dimethyl-1,3-propanediylbis(oxy)]-5(10)-estren-17β-ol (1H)

300 ml of liquid ammonia is condensed in a flask cooled to −70° C. A solution of 7.23 g of 1G in 50 ml of absolute tetrahydrofuran is instilled at −70° C. 521 mg of lithium is added by portions, then is stirred for 3 hours under protective gas at the same temperature. Then 1.5 ml of t-butanol is instilled and stirred for 2 more hours. After addition of 1.5 ml of iodomethane, it is heated to room temperature and diluted with water. The mixture is extracted with ethyl acetate. The organic phases are washed with water, dried on sodium sulfate and concentrated by evaporation in a vacuum. Column chromatography of the residue yields 4.34 g of 1H as white foam.

I. 11β-[4-(Dimethylamino)-phenyl]-3,3-[2,2-dimethyl-1,3-propanediylbis(oxy)]-5(10)-estren-17β-ol (1I)

Four spatula tips of Raney nickel are washed five times with methanol and mixed with a solution of 4.30 g of 1H in 200 ml of methanol. The reaction mixture is stirred for 16 hours under protective gas at room temperature. The solution is decanted, the residue is washed twice with methanol and three times with methylene chloride. The combined solutions are suctioned off over a frit and concentrated by evaporation in a vacuum. Column chromatography of the residue yields 2.35 g of 1I as white foam.

K. 11β-[4-(Dimethylamino)phenyl]-3,3-[2,2-dimethyl-1,3-propanediylbis(oxy)]-5(10)-estren-17-on (1K)

A solution of 2.3 g of 1I, 2.45 ml of cyclohexane and 350 mg of aluminum triisopropylate in 50 ml of toluene is boiled for 14 hours under protective gas on the water separator. The reaction mixture, after cooling, is mixed with water and extracted with ethyl acetate. The organic phase is washed with saturated sodium chloride solution, dried on sodium sulfate and concentrated by evaporation in a vacuum. The residue is chromatographed on aluminum oxide (neutral, stage III) with a mixture of hexane/ethyl acetate. 2.16 g of 1K is obtained as white foam.

L. 11β-[4-(Dimethylamino)phenyl]-3,3-[2,2-dimethyl-1,3-propanediylbis(oxy)]-17α-(1-propinyl-5(10)-estren-17β-ol (1L)

75 ml of absolute tetrahydrofuran is saturated by one-hour introduction of propine at 0° C. Then 16 ml of a 15% solution of butyllithium is instilled in hexane at 0° C. and stirred for one hour under protective gas. After instillation of a solution of 2.1 g of 1K it is stirred for 20 hours at room temperature. The reaction mixture is mixed with water and extracted with ethyl acetate. The combined organic phases are washed with saturated sodium chloride solution, dried on sodium sulfate and concentrated by evaporation in a vacuum. The residue is chromatographed on aluminum oxide (neutral, stage III) with a mixture of hexane/ethyl acetate. 2.13 g of 1L is obtained as white foam.

M. 11β-[4-(Dimethylamino)phenyl]-17β-hydroxy-17α-(1-propinyl)-5(10)-estren-3-one (1M).

2.11 g of 1L is dissolved in 100 ml of acetone, mixed with 17 ml of 4 n aqueous hydrochloric acid and stirred for 30 minutes under protective gas at room temperature. The reaction solution is neutralized with saturated sodium bicarbonate solution and extracted with ethyl acetate. The combined organic phases are washed with saturated sodium chloride solution, dried on sodium sulfate and concentrated by evaporation in a vacuum. Column chromatography of the residue yields 1.59 g of 1M as white foam.

N. 11β-[4-(Dimethylamino)phenyl]-17β-hydroxy-17α-(1-propinyl)-4-estren-3-one (1N)

509 mg of p-toluenesulfonic acid is heated to boiling in 95 ml of toluene under protective gas. 1.05 g of 1M, dissolved in 5 ml of toluene, is quickly added. It is stirred for 45 minutes at 110° C., then a few drops of triethylamine are added. After cooling, it is washed with sodium bicarbonate solution. The organic phase is dried on sodium sulfate and concentrated by evaporation in a vacuum. Column chromatography yields 223 mg of the title compound 1N as white foam.

$^1$H-NMR(CDCl$_3$) δ: 7.27 ppm(2H,d J=8 Hz, aromatic); 6.67 ppm(2H,d J=8 Hz, aromatic); 5.85 ppm(1H, s broad, H-4); 3.33 ppm (1H,dd, broad J=6.0 Hz and J=5.5 Hz, H11), 2.94 ppm(6H,s, H—NCH$_3$); 1.89 ppm(3H,s,H—CH$_3$—C≡C—); 0.67 ppm(3H,s,H-18). $[\alpha]_D^{20}$=17.0° (CHCl$_3$; c=0.505).

Compound 1I can also be produced according to the following instructions:

1.66 g of 2,2-dimethyl-1,3-propanediol, 0.87 ml of trimethoxymethane and 150 mg of p-toluenesulfonic acid are added to a solution of 2.5 g of 11β-[4-(dimethylamino)phenyl]-17β-hydroxy-5(10)-estren-3-one (production, see Tet. Let. 24, 5205 (1983)) in 18 ml of methylene chloride. The reaction mixture is stirred for 14 hours under protective gas at room temperature, diluted with methylene chloride and washed with sodium bicarbonate solution. The aqueous phase is extracted with methylene chloride. The combined organic phases are dried on sodium sulfate and concentrated by evaporation in a vacuum. Column chromatography of the residue yields 2.32 g of 1I.

Example 2

Production of 3,3-[2,2-dimethyl-1,3-propanediylbis(oxy)]-10β,11β-(5-methoxy-o-phenylenethio)-estrane-5α,17β-diol (2B)

A. 10β-[(2-Bromo-5-methoxyphenyl)thio]-3,3-[2,2-dimethyl-1,3-propanediylbis(oxy)]-9(11)-estr-ene-5α,17β-diol (2A)

The performance and working up takes place as described in example 1A. Amounts used: 12.73 g of 3,3-[2,2-dimethyl-1,3-propanediylbis(oxy)]-5α,10α-epoxy-estr-9(11)en-17β-ol in 100 ml of abs. tetrahydrofuran, 22.3 g of 2-bromo-5-methoxythiophenol in 182 ml of abs. tetrahydrofuran, 40 ml of 2.5 molar butyllithium solution in n-hexane. Column chromatography yields 17.99 g of 2A. Mp: 117°–119° C.

B. 3,3-[2,2-Dimethyl-1,3-propanediylbis(oxy)]-10β,11β-(5-methoxy-o-phenylenethio)-estran-5α,17β-diol (2B)

Performance and working up takes place as in example 1G.

Yield: 1.09 g of 2B, Mp: 95°–97° C.

Example 3

Production of 11β-[4-(dimethylamino)phenyl]-17β-hydroxy-17α-(3-hydroxy-1Z-propenyl-4-estren-3-one (3E)

A. 11β-[4-(Dimethylamino)phenyl]-17β-hydroxy-4-estren-3-one (3A)

A solution of 2.7 g of 11β-[4-(dimethylamino)phenyl]-17β-hydroxy-5(10)-estren-3-one (production see Tet. Let. 24, 5205 (1983)) in 270 ml of methylene chloride is heated to boiling with 3.91 g of p-toluenesulfonic acid for one day under protective gas, then a few drops of triethylamine are added. After cooling, it is washed with sodium bicarbonate solution. The organic phase is dried on sodium sulfate and concentrated by evaporation in a vacuum. Column chromatography yields 1.85 g of 3A as white foam.

B. 11β-[4-(Dimethylamino)phenyl]-3,3-[1,2-ethanediylbis(thio)]-4-estren-17β-ol (3B)

0.11 ml of 1,2-ethanedithiol and 3.62 mg of p-toluenesulfonic acid are added to a solution of 500 mg of 3A in 5 ml of glacial acetic acid. The reaction mixture is stirred for one hour at room temperature under protective gas and then made basic with 2N aqueous sodium hydroxide solution. The aqueous phase is extracted with ethyl acetate. The combined organic phases are washed with saturated sodium bicarbonate solution, dried on sodium sulfate and concentrated by evaporation in a vacuum. Column chromatography yields 399 mg of 3B.

C. 11β-[4-(Dimethylamino)phenyl]-3,3-[1,2-ethanediylbis(thio)-4-estren-17-one (3C)

A solution of 390 mg of 3B, 0.42 ml of cyclohexanone and 76 mg of aluminum triisopropylate in 10 ml of toluene is boiled for 30 hours under protective gas on the water separator. After cooling, the reaction mixture is mixed with water and extracted with ethyl acetate. The organic phase is washed with saturated sodium bicarbonate solution, dried on sodium sulfate and concentrated by evaporation in a vacuum. Column chromatography yields 330 mg of 3C as white foam.

D. 11β-[4-(Dimethylamino)phenyl]-3,3-[1,2-ethanediylbis(thio)-17α-[3-(tetrahydro-2H-pyran-2-yl)oxy]-1-propinyl]-4-estren-17β-ol (3D)

A solution of 0.89 ml of 2-(2-propinyloxy)tetrahydro-2H-pyrane in 30 ml of tetrahydrofuran is mixed with a solution of 3.66 ml of a 15% solution of butyllithium in hexane at 0° C. and stirred for 30 minutes at 0° C. under protective gas. Then a solution of 280 mg of 3C in 10 ml of tetrahydrofuran is instilled at the same temperature. Then it is stirred at 0° C. for two hours. The reaction mixture is mixed with ammonium chloride solution and extracted with ethyl acetate. The combined organic phases are washed with sodium chloride solution, dried on sodium sulfate and concentrated by evaporation in a vacuum. Column chromatography yields 328 mg of 3D as white foam.

E. 11β-[4-(Dimethylamino)phenyl]-17β-hydroxy-17α-(3-hydroxy-1-propinyl-4-estren-3-one (3E)

300 mg of 3D as well as 2.21 g of glyoxylic acid hydrate are dissolved in 18 ml of glacial acetic acid. The reaction mixture is stirred for 1.5 minutes under protective gas at room temperature, mixed with 2.1 ml of 4N aqueous hydrochloric acid and stirred for 10 more minutes. Then it is neutralized with sodium bicarbonate solution and extracted with ethyl acetate. The combined organic phases are washed with sodium chloride solution, dried on sodium sulfate and concentrated by evaporation in a vacuum. Column chromatography yields 135 mg of 3E.

Crystallization from ethyl acetate/hexane leads to 112 mg of said compound. Mp: 142°–145° C.: $[\alpha]_D^{20}$ =+4.0° (CHCl$_3$: c=1.000)

F. 11β-[4-(Dimethylamino)phenyl]-17β-hydroxy-17α-(3-hydroxy-1Z-propenyl)-4-estren-3-one (3F)

A solution of 78 mg of 3E in 2 ml of ethanol and 2 ml of pyridine is hydrogenated for 3 hours in the presence of 13 mg of 10% Pd/BaSO$_4$ catalyst. The reaction mixture is suctioned off over Celite and rewashed with ethanol and methylene chloride. The filtrate is concentrated by evaporation in a vacuum. The residue is chromatographed on silica gel with a mixture of methylene chloride/methanol. 63 mg of 3F is isolated as white foam.

$^1$H-NMR(CD$_2$Cl$_2$) δ: 7.27 ppm (2H,d J=9 Hz, H-aromatic); 6.67 ppm (2H, d J=9 Hz,H aromatic); 5.78 ppm (1H,s broad,H-4); 5.68 ppm(1H,ddd J=12,5 Hz and J=5.0 Hz and J=4.5 Hz,H—CH=); 5.63 ppm(1H,d J=12.5 Hz,H—CH=); 4.32 ppm(1H,dd J=13.0 Hz and J=5.0 Hz); 3.28 ppm(1H,dd broad J=6.0 Hz and J=5.0 Hz,H-11); 2.92 ppm (6H,s,H—NCH$_3$); 0.71 ppm(3H,dH-18).

Example 4

Production of 11β-(4-acetylphenyl)-17β-hydroxy-17α-(1-propinyl)-4-estren-3-one (4K)

A. 17β-Hydroxy-11β-(4-hydroxyphenyl)-5(10)-estren-3-one (4A)

3.27 g of sodium methane thiolate is added to a solution of 5 g of 17β-hydroxy-11β-(4-methoxyphenyl)-5(10)-estren-3-one (production see Tet. Let. 24, 5205 (1983)) in 50 ml of abs. N,N-dimethylformamide. The reaction mixture is stirred for 90 minutes at 160° C. After cooling, it is diluted with water and extracted with ethyl acetate. The organic phase is washed with saturated sodium bicarbonate solution, dried on sodium sulfate and concentrated by evaporation in a vacuum. Column chromatography yields 4.29 g of 4A as white foam.

B. 3,3-[2,2-Dimethyl-1,3-propanediylbis(oxy)]-11β-(4-hydroxyphenyl)-5(10)-estren-17β-ol (4B)

A solution of 4.2 g of 4A, 1.72 g of 2,2-dimethyl-1,3-propanediol, 1.5 ml of trimethoxymethane and 250 mg of p-toluenesulfonic acid in 40 ml of methylene chloride is stirred for 14 hours under protective gas at room temperature. Then saturated sodium bicarbonate solution is added. The aqueous phase is extracted with methylene chloride. The combined organic phases are dried on sodium sulfate and concentrated by evaporation in a vacuum. Column chromatography leads to 3.25 g of 4B as white foam.

C. 3,3-[2,2-Dimethyl-1,3-propanediylbis(oxy)]-11β-[4-[[(trifluoromethyl)sulfonyl]oxy]phenyl]-5(10)-estren-17β-ol (4C)

A solution of 1.86 ml of trifluoromethane sulfonic acid anhydride in 10 ml of methylene chloride is instilled into a solution of 3.2 g of 4B and 4.75 of 4-(dimethylamino)pyridine in 100 ml of methylene chloride at −78° C. under protective gas. The reaction mixture is stirred for 2 hours more at −78° C. and then poured into saturated sodium bicarbonate solution. The aqueous phase is extracted with methylene chloride. The combined organic phases are washed with water, dried on sodium sulfate and concentrated by evaporation in a vacuum. Column chromatography yields 2.9 of 4C as white foam.

D. 11β-(4-Acetylphenyl)-3,3-[2,2-dimethyl-1,3-propanediylbis(oxy)]-5(10)-estren-17β-ol (4D)

A solution of 2.84 g of 4C in 35 ml of N,N-dimethylformamide is mixed with 393 mg of lithium chloride and is stirred for 15 minutes under protective gas at room temperature. Then 277 mg of tetrakis (triphenylphosphine)palladium(O) and 1.7 ml of (1-ethoxyethenyl)tributylstannane are added. The reaction mixture is stirred for 3 hours at 110° C., after cooling is diluted with 120 ml of ethyl acetate and suctioned off over Celite. The filtrate is washed four times with saturated sodium chloride solution, dried on sodium sulfate and concentrated by evaporation in a vacuum. Column chromatography yields 1.79 g of 4D, white foam.

E. 11β-(4-Acetylphenyl)-17β-hydroxy-5(10)-estren-3-one (4E)

1.7 g of 4D is dissolved in 100 ml of acetone, mixed with 5.4 ml of 4 n aqueous hydrochloric acid and stirred for one hour under protective gas at room temperature. The reaction solution is neutralized with saturated sodium bicarbonate solution and extracted with ethyl acetate. The combined organic phases are washed with saturated sodium chloride solution, dried on sodium sulfate and concentrated by evaporation in a vacuum. Column chromatography yields 1.31 g of 4E, white foam.

F. 11β-(4-Acetylphenyl)-17β-hydroxy-4-estren-3-one (4F)

485 mg of p-toluenesulfonic acid is heated to 90° C. in 100 ml of toluene under protective gas. 500 mg of 4E, dissolved in 5 ml of toluene, is quickly added. The reaction mixture is stirred for one hour at 90° C. and after cooling is mixed with saturated sodium bicarbonate solution. The aqueous phase is extracted with ethyl acetate. The combined organic phases are washed over sodium sulfate and concentrated by evaporation in a vacuum. The residue is chromatographed on silica gel with ethyl acetate/hexane. 239 mg of the title compound 4F is obtained as white foam.

$^1$H-NMR(CDCl$_3$) δ: 7.90 ppm (2H,d J=8 Hz,H-aromatic); 7.54 ppm (2H,d J=8 Hz, H-aromatic); 5.87 ppm (1H,s,H-4); 3.61 ppm (1H,dd broad J=9.0 Hz and J=7.5 Hz,H-17); 3.42 ppm (1H,dd broad J=6.0 Hz and J=5.5 Hz,H-11); 2.61 ppm (3H,s,H—Ac); 0.52 ppm (3H,s,H-18).

G. 3,3-[1,2-Ethanediylbis(thio)]-11β[4-(2-methyl-1,3-dithiolan-2-yl)phenyl]-4-estren-17β-ol (4G)

0.90 ml of 1,2-ethanedithiol and 1.18 g of p-toluenesulfonic acid are added to a solution of 2.12 g of 4F. The reaction mixture is stirred for five hours at room temperature under protective gas and then made basic with 2M aqueous sodium hydroxide solution. The aqueous phase is extracted with ethyl acetate. The combined organic phases are washed with saturated sodium bicarbonate solution, dried on sodium sulfate and concentrated by evaporation in a vacuum. The crude product is dissolved in 80 ml of methylene chloride and 160 ml of ethanol and refluxed for six hours with 1.49 g of solid potassium carbonate. The cooled solution is filtered and concentrated by evaporation. Column chromatography yields 2.02 g of 4G as white foam.

H. 3,3-[1,2-ethanediylbis(thio)]-11β[4-(2-methyl-1,3-dithiolan-2-yl)phenyl]-4-estren-17-one (4H)

As described under 3C 1.81 g of 4H is produced from 1.95 g of 4G with 2.42 ml of cyclohexanone and 438 mg of aluminum triisopropylate in 35 ml of toluene.

IR (KBr): 1740 cm$^{-1}$ (C=O)

I. 3,3-[1,2-ethanediylbis(thio)]-11β[4-(2-methyl-1,3-dithiolan-2-yl)phenyl]-17α-(1-propinyl)-4-estren-17β-ol (4I)

As described under IL, 779 mg of 4I is produced from 763 mg of 4H with 5.8 ml of a 15% solution of butyllithium in hexane in 50 ml of tetrahydrofuran saturated with propine.

IR(KBr): 2240 cm$^{-1}$ (C≡C).

K. 11β-(4-Acetylphenyl)-17β-hydroxy-17α-(1-propinyl)-4-estren-3-one (4K)

1.28 g of N-chlorosuccinimide and 1.83 g of silver(I) nitrate are put in 50 ml of an acetonitrile/water mixture (8:2). A solution of 700 mg of 4I in 3 ml of acetone and 2 ml of acetonitrile is rapidly instilled at room temperature under protective gas. After 15 minutes it is mixed with successively with saturated sodium sulfite solution, saturated sodium carbonate solution and saturated sodium chloride solution as well as methylene chloride. The mixture is filtered over Celite, dried on sodium sulfate and concentrated by evaporation in a vacuum. Column chromatography yields 238 mg of the title compound of 4K as pale yellow foam.

IR (KBr): 2235 cm$^{-1}$ (C≡C), 1678 cm$^{-1}$ (C=O), 1664 cm$^{-1}$ (C=O).

$^1$H-NMR(CDCl$_3$) δ: 7.90 ppm (2H,d J=9 Hz,H aromatic); 7.54 ppm (2H,d J=9 Hz,H-aromatic); 5.88 ppm (1H,s,broad, H-4); 3.48 ppm (1H,dd broad J=6.5 Hz and J=6.0 Hz,H-11); 2.80 ppm (1H,m,H-10); 2.60 ppm (3H,s,H—Ac); 1.89 ppm (3H,s,H—CH$_3$—C≡C—); 0.59 ppm (3H,s,H-18).

Example 5

Production of (Z)-11β-(4-acetylphenyl)-17β-hydroxy-17α-(3-hydroxy-1-propenyl)-4-estren-3-one (5C)

A. 3,3-[1,2-Ethanediylbis(thio)]-11β-[4-(2-methyl-1,3-dithiolan-2-yl)phenyl]-17α[3-[(tetrahydro-2H-pyran-2-yl)oxy]-1-propinyl-4-estren-17β-ol As described under 3D, 1.19 g of 5A is produced from 1.0 g of 4H with 2.74 ml of 2(2-propinyloxy)tetrahydro-2H-pyrane and 11.3 ml of a 15% solution of butyllithium in hexane in 120 ml of tetrahydrofuran.

B. 11β-(4-Acetylphenyl)-17β-hydroxy-17α-(3-hydroxy-1-propinyl)-4-estren-3-one (5B)

As described under 4K, 1.73 g of 5A is reacted with 2.71 g of N-chlorosuccinimide and 3.87 g of silver(I) nitrate in 10 ml of acetone, 24 ml of water and 96 ml of acetonitrile. The crude product is stirred with 127 mg of pyridinium p-toluenesulfonate in 15 ml of moist ethanol for two hours at 60° C. The solution is concentrated by evaporation to half volume, diluted with ethyl acetate, washed with half-saturated sodium chloride solution and water, dried on sodium sulfate and concentrated by evaporation in a vacuum. Column chromatography yields 265 mg of 5B as pale yellow foam.

IR(KBr): 2235 cm$^{-1}$ (C≡C), 1678 cm$^{-1}$ (C=O), 1665 cm$^{-1}$ (C=O).

$^1$H-NMR(CDCl$_3$) δ: 7.91 ppm (2H,d J=9 Hz,H aromatic); 7.54 ppm (2H,d J=9 Hz,H-aromatic); 5.88 ppm (1H,s,broad, H-4); 4.37 ppm (2H,s,broad,H—CH$_2$OH) ;3.48 ppm (1H,dd broad J=6.0 Hz and J=5.0 Hz,H-11); 2.81 ppm (1H,m,H-10);2.61 ppm (3H,s,H—Ac); 0.62 ppm (3H,s,H-18).

C. (Z)-11β-(4-Acetylphenyl)-17β-hydroxy-17α-(3-hydroxy-1-propenyl)-4-estren-3-one (5C)

As described under 3F, 245 mg of 5B is hydrogenated with 60 mg of 10% Pd/BaSO$_4$ catalyst in 4 ml of pyridine and 4 ml of ethanol. After silica gel chromatography, 170 mg of the title compound 5C is obtained. Crystallization from methylene chloride/diisopropyl ether yields 146 mg of 5C as light yellow crystals.

Mp: 225°–230° C.; [α]$_D^{22}$=+76.4° (CHCl$_3$; c=0.500)
IR(KBr): 1680 cm$^{-1}$ (C=O),1665 cm$^{-1}$ (C=O).

Example 6

Production of 11β-[4-(dimethylamino)phenyl]-17α-(1-propinyl)-4-estren-17β-ol (6C)

A. 11β-[4-(Dimethylamino)phenyl]-4-estren-17β-ol (6A)

120 ml of liquid ammonia is condensed in a flask cooled to −75° C. 91 mg of lithium is added. After 20 minutes, a solution of 770 mg of 3B is instilled in 4 ml of tetrahydrofuran. 182 mg of lithium is added by portions, then is stirred for two hours at −75° C. Then 9 ml of ethanol is instilled. The batch is allowed to stand overnight at room temperature, then diluted with water. The mixture is extracted with ethyl acetate. The organic phases are washed with saturated sodium chloride solution, dried on sodium sulfate and concentrated by evaporation in a vacuum. Silica gel chromatography of the residue yields 350 mg of 6A as white foam.

$^1$H-NMR(CD$_2$Cl$_2$) δ: 7.27 ppm (2H,d J=9 Hz,H-aromatic); 6.63 ppm (2H,d J=9 Hz,H-aromatic); 5.40 ppm (1H,s,broad,H-4); 3.51 ppm (1H,dd, broad J=9 Hz and J=6 Hz,H-17); 3.22 ppm (1H,dd broad J=6 Hz and J=5 Hz,H-11); 2.91 ppm (6H,s,H—NCH$_3$); 2.46 ppm (1H,m,H-10);0.50 ppm (3H,s,H-18).

B. 11β-[4-(Dimethylamino)phenyl]-4-estren-17-one (6B)

As described under 3C, 225 mg of 6B is produced from 327 mg of 6A with 400 microliters of cyclohexanone and 409 of aluminum triisopropylate in 10 ml of toluene.

IR (KBr): 1740 cm$^{-1}$ (C=O).

$^1$H-NMR(CD$_2$Cl$_2$) δ: 7.28 ppm (2H,d J=9 Hz,H-aromatic); 6.64 ppm (2H,d J=9 Hz,H-aromatic); 5.43 ppm (1H,s broad,H-4); 3.29 ppm (1H,dd,broad J=5.5 Hz and J=5 Hz,H-11); 2.91 ppm (6H,s,H—NCH$_3$); 2.50 ppm (1H,m,H-10); 0.63 ppm (3H,s,H-18).

C. 11β-[4-(Dimethylamino)phenyl]-17α-(1-propinyl)-4-estren-17β-ol (6C)

As described under IL, 207 mg of 6C is produced from 215 mg of 6B with 2.1 ml of a 15% solution of butyllithium in hexane in 20 ml of tetrahydrofuran saturated with propine. Crystallization from pentane/ethyl acetate leads to 168 mg of said compound.

Mp: 187° C., [α]$_D^{22}$=28.3° (CHCl$_3$; c=0.505).
IR(KBr): 2240 cm$^{-1}$ (C≡C).

Example 7

Production of (Z)-17β-hydroxy-17α(3-hydroxy-1-propenyl)-11β-[4-(3-pyridinyl)phenyl]-4-estren-3-one (7I)

A. 3,3-[2,2-Dimethyl-1,3-propanediylbis(oxy)]-11β-[4-(3-pyridinyl)phenyl]-5(10)-estren-17β-ol (7A) and
B. 3,3-[2,2-dimethyl-1,3-propanediylbis(oxy)]-11β-(4-ethylphenyl)-5(10)-estren-17β-ol (7B)

747 mg of diethyl(3-pyridinyl)borane (Aldrich), 392 mg of lithium chloride, 6 ml of 2M sodium carbonate solution and 267 mg of tetrakis(triphenylphosphine)palladium(O) are added to a solution of 2.71 g of 4C in 40 ml of toluene and 18 ml of ethanol under protective gas. The mixture is heated for two hours to 95° C. and, after cooling, is taken up in ethyl acetate. The organic phase is washed with saturated sodium chloride solution, dried on sodium sulfate and concentrated by evaporation in a vacuum. After column chromatography 1.94 g of 7A as well as 171 mg of 7B are obtained.

C. 17β-Hydroxy-11β-[4-(3-pyridinyl)phenyl]-5(10)-estren-3-one (7C)

As described under 4E, 1.07 g of 7C is produced from 1.9 g of 7A with 7 ml of 4M aqueous hydrochloric acid in 150 ml of acetone.

D. 17β-Hydroxy-11β-[4-(3-pyridinyl)phenyl]-4-estren-3-one (7D)

1.06 g of 7C is dissolved in 20 ml of chloroform, mixed with 944 mg of p-toluenesulfonic acid under protective gas and refluxed for three hours. The cooled solution is mixed with a few drops of triethylamine, diluted with methylene chloride, washed with saturated sodium chloride solution, dried on sodium sulfate and concentrated by evaporation in a vacuum. Silica gel chromatography yields 644 mg of 7D.

IR(KBr): 1667 cm$^{-1}$ (C=O).

$^1$H-NMR(CDCl$_3$) δ: 8.87 ppm (1H,d broad J=2 Hz,H-Py2); 8.58 ppm (1H,dd broad J=5.0 Hz and J=2 Hz,H-Py6); 7.89 (1H,ddd J=8 Hz and J=2 Hz and J=2 Hz,H-Pyd4); 7.54 ppm (4H,m,H-aromatic); 7.37 ppm (1H,dd broad J=8 Hz and J=5.0 Hz,H-Py5); 5.88 ppm (1H,s,broad,H-4); 3.61 ppm (1H,dd broad J=9.0 Hz and J=7.0 Hz,H-17); 3.40 ppm (1H,dd broad J=6.0 Hz and J=5.0 Hz,H-11); 2.86 ppm (1H,m,H-10); 0.58 ppm (3H,s,H-18).

E. 3,3-[1,2-Ethanediylbis(thio)]-11β[4-(3-pyridinyl)phenyl]-4-estren-17β-ol (7E)

As described under 4G, 569 mg of 7E is produced from 629 mg of 7D with 123 microliters of 1,2-ethanedithiol and 419 mg of p-toluenesulfonic acid in 6 ml of glacial acetic acid as well as with 203 mg of potassium carbonate in 8 ml of methylene chloride and 45 ml of methanol.

F. 3,3-[1,2-Ethanediylbis(thio)]-11β[4-(3-pyridinyl)phenyl]-4-estren-17-one (7F)

As described under 3C, 460 mg of 7F is produced from 550 mg of 7E with 510 microliters of cyclohexanone and 100 mg of aluminum triisopropylate in 17 ml of toluene.

IR(KBr): 1736 cm$^{-1}$ (C=O).

G. 3,3-[1,2-Ethanediylbis(thio)]-11β[4-(3-pyridinyl)phenyl]-17α-[3-[tetrahydro-2H-pyran-2-yl)oxy]-1-propinyl]-4-estren-17β-ol (7G)

As described under 3D, 460 mg of 7G is produced from 442 mg of 7F with 1.30 ml of 2-(2-propinyloxy)tetrahydro-2H-pyrane and 5.36 ml of a 15% solution of butyllithium in hexane in 70 ml of tetrahydrofuran.

H. 17β-Hydroxy-17α-(3-hydroxy-1-propinyl)-11β-[4-(3-pyridinyl)phenyl]-4-estren-3-one (7H)

As described under 3E, 234 mg of 7H is produced from 453 mg of 7G with 3.27 g of glyoxylic acid and 2.98 ml of 4M aqueous hydrochloric acid in 8 ml of acetone and 8 ml of glacial acetic acid.

$^1$H-NMR(CDCl$_3$) δ: 8.88 ppm (1H, d broad J=2 Hz, H-Py2); 8.59 ppm (1H, dd broad J=4.5 Hz and J=2 Hz,H=Py6); 7.90 ppm (1H,ddd J=8 Hz and J=2 Hz and J=2 Hz,H-Py4); 7.53 ppm (4H,m,H-aromatic); 7.38 ppm (1H,dd broad J=8 Hz and J-4.5 Hz,H-Py5); 5.89 ppm (1H,s,broad, H-4); 4.38 ppm (2H,m,H—CH$_2$OH); 3.48 ppm (1H,dd broad J=6.0 Hz and J=5.0 Hz,H-11); 2.88 ppm (1H,m,H-10); 0.68 ppm (3H,s,H-18).

I. (Z)-17β-Hydroxy-17α(3-hydroxy-1-propenyl)-11β-[4-(3-pyridinyl)phenyl]-4-estren-3-one (7I)

As described under 3F, 225 mg of 7H is hydrogenated with 45 mg of 10% Pd/BaSO$_4$ catalyst in 2 ml of pyridine and 4 ml of ethanol. After silica gel chromatography, 160 mg of the title compound 7I is obtained.

IR (KBr): 1663 cm$^{-1}$ (C=O).

$^1$H-NMR(CDCl$_3$) δ: 8.88 ppm (1H, d broad J=2 Hz,H-Py2); 8.59 ppm (1H, dd broad J=4.5 Hz and J=2 Hz,H-Py6); 7.52 ppm (1H,ddd J=8 Hz and J=2 Hz and J=2Hz,H-Py4); 7.52 ppm (4H,m,H-aromatic); 7.40 ppm (1H,dd broad J=8 Hz and J=4.5 Hz, H-Py5); 5.88 ppm (1H,s,broad,H-4); 5.72 ppm (1H,ddd J=11.5 Hz and J=5.5 Hz and J=5.5 Hz,H—CH=); 5.65 ppm (1H,d broad J=11.5 Hz,H—CH=) ;4.28 ppm (2H,m,H—CH$_2$OH); 3.24 ppm (1H,dd broad J=6.0 Hz and J=4.5 Hz, H-11); 2.87 ppm (1H,m,H-10); 0.73 ppm (3H,s,H-18).

Example 8

Production of 17β-hydroxy-3-oxo-11β-[4-(-pyridinyl)phenyl]-4-estrene-17α-acetonitrile (8B)

A. 3,3-[1,2-Ethanediylbis(thio)]-17β-hydroxy-11β-[4-(3-pyridinyl)phenyl]-4-estrene-17α-acetonitrile (8A)

13.7 ml of a 15% solution of butyllithium in hexane is instilled in a solution of 3.31 ml of diisopropylamine in 100 ml of tetrahydrofuran at −78° C. under protective gas. After 30 minutes, 1.13 ml of acetonitrile is added at the same temperature. 15 minutes later, a solution of 1.00 g of 7E in 90 ml of tetrahydrofuran is instilled at the same temperature and stirred for two more hours. Then it is mixed with saturated ammonium chloride solution and extracted with ethyl acetate. The combined organic phases are washed with water, dried on sodium sulfate and concentrated by evaporation in a vacuum. Column chromatography yields 1.05 g of 8A.

B. 17β-Hydroxy-3-oxo-11β-[4-(3-pyridinyl)phenyl]-4-estrene-17α-acetonitrile (8B)

As described under 3E, 644 mg of 8B is produced from 1.04 g of 8A with 7.51 g of glyoxylic acid and 6.85 ml of 4M aqueous hydrochloric acid in 18 ml acetone and 18 ml glacial acetic acid. 597 mg of said compound is obtained by crystallization from ethyl acetate/hexane.

Mp: 173°–174° C.; [α]$_D^{22}$=+131.8° (CHCl$_3$; c=0.500).
IR(KBr): 2245 cm$^{-1}$ (C≡C), 1664 cm$^{-1}$ (C=O).

Example 9

Production of (E)-17β-hydroxy-3-(hydroxyimino)-11β-[4-(3-pyridinyl)phenyl]-4-estrene-17α-acetonitrile (9A) and (Z)-17β-hydroxy-3-(hydroxyimino)-11β-[4-(3-pyridinyl)phenyl]-4-estrene-17α-acetonitrile A. (E)-17β-hydroxy-3-(hydroxyimino)-11β-[4-(3-pyridinyl)phenyl]-4-estrene-17α-acetonitrile (9A) and B. (Z)-17β-hydroxy-3-(hydroxyimino)-11β-[4-(3-pyridinyl)phenyl]-4-estrene-17α-acetonitrile (9B)

219 mg of 8B is stirred with 50 mg of hydroxyl ammonium chloride in 5 ml of pyridine under protective gas for 90 minutes at 50° C. The reaction mixture is taken up in water and extracted with methylene chloride. The organic phase is washed with water, dried on sodium sulfate and concentrated by evaporation in a vacuum. After column chromatography and crystallization from methylene chloride/diisopropyl ether, there are obtained 97 mg of 9A [Mp: 227°–229° C.; [α]$_D^{22}$ =+192.4° (CHCl$_3$/MeOH; c=0.500); IR(KBr): 2250 cm$^{-1}$ (C≡N), 1635 cm$^{-1}$ (C=NOH)] as well as 61 mg of 9B [Mp: 198°–200° C.; [α]$_D^{22}$=+230.4° (CHl$_3$; c=0.500); IR(KBr):2250cm$^{-1}$ (C≡N), 1635 cm$^{-1}$ (C=NOH)].

Example 10

Production of 17β-hydroxy-17α-(2-propenyl)-11β-[4-(3-pyridinyl)phenyl]-4-estren-3-one (10B)

A. 3,3-[1,2-ethanediylbis(thio)]-17α-(2-propenyl)-11β-[4-(3-pyridinyl)phenyl]-4-estren-17β-ol (10A)

414 mg of magnesium chips are put into 5 ml of diethyl ether under protective gas. 150 microliters of 3-bromo-1-propene and some crystals of iodine are added, then a solution of 2.00 g of 7F and 1.32 g of 3-bromo-1-propene in 40 ml of diethyl ether and 10 ml of tetrahydrofuran is instilled and refluxed for three hours. Saturated ammonium chloride solution is added for working up and it is extracted with ethyl acetate. The organic phase is washed with saturated sodium chloride solution, dried on sodium sulfate and concentrated by evaporation in a vacuum. Column chromatography yields 1.63 g of 10A.

B. 17β-Hydroxy-17α-(2-propenyl)-11β-[4-(3-pyridinyl)phenyl]-4-estren-3-one (10B)

As described under 3E, 592 mg of 10B is produced from 1.44 g of 10A with 10.35 g of glyoxylic acid and 9.40 ml of 4M aqueous hydrochloric acid in 25 ml of acetone and 25 ml of glacial acetic acid. By crystallization from ethyl acetate/hexane 483 mg of said compound is obtained.

Mp: 127°–128° C.; $[α]_D^{22}$=+128.7° (CHCl$_3$;c=0.470). IR(KBr): 1668 cm$^{-1}$ (C=O).

Example 11

Production of 17β-hydroxy-17α-(methoxymethyl)-11β-[4-(3-pyridinyl)phenyl]-4-estren-3-one (11C)

A. (11β,17β) 3,3-[1,2-Ethanediylbis(thio)]-11β[4-(3-pyridinyl)phenyl]spiro[estr-4-en-17,2'-oxirane] (11A)

2.5 g of 7E to stirred with 4.12 g of trimethylsulfonium iodide and 2.75 g of potassium tert-butylate in 100 ml of dimethylformamide under protective gas for 30 minutes at room temperature. Then water is added with ice-bath cooling and extraction with ethyl acetate is performed. The organic phase is washed with saturated sodium chloride solution, dried on sodium sulfate and concentrated by evaporation in a vacuum. Column chromatography yields 866 mg of 11A.

B. 3,3-[1,2-ethanediylbis(thio)]-17α-(methoxymethyl)-11β-[4-(3-pyridinyl)phenyl]-4-estren-17β-ol (11B)

1.20 g of sodium is dissolved in 15 ml of methanol. A solution of 842 mg of 11A is instilled in 20 ml of methanol. The reaction mixture is heated to boiling for five hours. Then the methanol is largely concentrated by evaporation. The residue is taken up in water and extracted with methylene chloride. The organic phase is washed with saturated sodium chloride solution, dried on sodium sulfate and concentrated by evaporation in a vacuum. Column chromatography yields 486 mg of 11B.

C. 17β-Hydroxy-17α-(methoxymethyl)-11β-[4-(3-pyridinyl)phenyl]-4-estren-3-one (11C)

As described under 3E, 252 mg of 11C is produced from 470 mg of 11B with 3.38 g of glyoxylic acid and 3.00 ml of 4M aqueous hydrochloric acid in 8 ml acetone and 8 ml of glacial acetic acid. By crystallization from ethyl acetate/hexane 204 mg of said compound is obtained.

Mp: 145°–146° C.; $[α]_D^{22}$=+120.8° (CHCl$_3$; c=0.465). IR(KBr): 1665 cm$^{-1}$ (C=O).

Example 12

Production of 11β-(4-ethylphenyl)-17β-hydroxy-17α-(1-propinyl)-4-estren-3-one (12F)

A. 11β-(4-ethylphenyl)-17β-hydroxy-5(10)-estren-3-one (12A)

As described under 4E, 576 mg of 12A is produced from 863 mg 7B with 3 ml of 4M aqueous hydrochloric acid in 70 ml of acetone.

B. 11β-(4-ethylphenyl)-17β-hydroxy-4-estren-3-one (12B)

As described under 7D, 433 mg of 12B is produced from 568 mg of 12A with 500 mg of p-toluenesulfonic acid in 10 ml of chloroform.

IR(KBr): 1665 cm$^{-1}$(C=O).

$^1$H-NMR(CDCl$_3$+Py-d$_5$) δ: 7.31 ppm (2H,d J=9 Hz,H-aromatic); 7.10 ppm (2H,d J-9 Hz,H-aromatic); 5.84 ppm (1H,s,broad,H-4); 3.59 ppm (1H,dd,broad J=9.0 Hz and J=7.5 Hz,H-17); 3.33 ppm (1H,dd,broad J=6.0 Hz and J=5.0 Hz,H-11);2.85 ppm (1H,m,H-10); 2.62 ppm (2H,q J-7.5 Hz, H—Et); 1.23 ppm (2H,t J=7.5 Hz,H—Et);0.55 ppm (3H,s, H-18).

C. 3,3-[1,2-Ethanediylbis(thio)]-11β(4-ethylphenyl)-4-estren-17β-ol (12C)

As described under 4G, 399 mg of 12C is produced from 433 mg of 12B with 85 microliters of 1,2-ethanedithiol and 285 mg of p-toluenesulfonic acid in 5 ml of glacial acetic acid as well as with 140 mg of potassium carbonate in 6 ml of methylene chloride and 30 ml of methanol.

D. 3,3-[1,2-Ethanediylbis(thio)]-11β-(4-ethylphenyl)-4-estren-3-one (12D)

As described under 3C, 347 mg of 12D is produced from 390 mg of 12C with 360 microliters of cyclohexanone and 70 mg of aluminum triisopropylate in 15 ml of toluene. IR(KBr): 1740 cm$^{-1}$ (C=O).

E. 3,3-[1,2-Ethanediylbis(thio)]-11β-(4-ethylphenyl)-17α-(1-propinyl)-4-estren-17β-ol (12E)

As described under II, 99 mg of 12E is produced from 100 mg of 12D with 800 microliters of a 15% solution of butyllithium in hexane in 10 ml of tetrahydrofuran saturated with propine.

IR(KBr): 2235 cm$^{-1}$ (C≡C).

F. 11β-(4-ethylphenyl)-17β-hydroxy-17α-(1-propinyl)-4-estren-3-one (12F)

As described under 3F, 34 mg of 12F is produced from 89 mg of 12E with 64 mg of glyoxylic acid and 600 microliters of 4M aqueous hydrochloric acid in 2 ml of acetone and 2 ml of glacial acetic acid after crystallization from methylene chloride/hexane.

Mp: 195°–196° C.; $[α]_D^{22}$=−17.9° (CHCl$_3$; c=0.485). IR(KBr): 2240 cm$^{-1}$ (C≡C), 1655 cm$^{-1}$ (C=O).

Example 13

Production of (Z)-11β-(4-ethylphenyl)-17β-hydroxy-17α-(3-hydroxy-1-propenyl)-4-estren-3-one (13C)

A. 3,3-[1,2-Ethanediylbis(thio)]-11β-(4-ethylphenyl)-17α-[3-[tetrahydro-2H-pyran-2-yl)oxy]-1-propinyl-4-estren-17β-ol (13A)

As described under 3D, 241 mg of 13A is produced from 235 mg of 12D with 0.70 ml of 2-(2-propinyloxy)tetrahydro-2H-pyrane and 2.90 ml of a 15% solution of butyllithium in hexane in 40 ml of tetrahydrofuran.

B. 11β-(4-Ethylphenyl)-17β-hydroxy-17α-(3-hydroxy-1-propinyl)-4-estren-3-one (13B)

As described under 3E, 13B is produced from 230 mg of 13A with 1.60 g of glyoxylic acid and 1.50 ml of 4M aqueous hydrochloric acid in 5 ml of acetone and 5 ml of glacial acetic acid.

IR(KBr): 2230 cm$^{-1}$ (C≡C), 1660 cm$^{-1}$ (C=O).

C. (Z)-11β-(4-ethylphenyl)-17β-hydroxy-17α-(3-hydroxy-1-propenyl)-4-estren-3-one (13C)

As described under 3F, 115 mg of 13B is hydrogenated with 25 mg of 10% Pd/BaSO$_4$ catalyst in 1 ml of pyridine and 4 ml of ethanol. After silica gel chromatography and crystallization from methylene chloride/hexane 76 mg of title compound 13C is obtained.

Mp: 98°–101° C., $[α]_D^{22}$=+76.6° (CHCl$_3$; c=0.500). IR(KBr): 1665 cm$^{-1}$ (C=O)

Example 14

Production of (Z)-11β-[4-(3-furanyl)phenyl]-17β-hydroxy-17α-(3-hydroxy-1-propenyl)-4-estren-3-one (14D)

A. 3,3-[2,2-dimethyl-1,3-propanediylbis(oxy)]-11β-[4-(3-furanyl)phenyl]-5(10)-estren-17β-ol (14A)

6.43 g of (3-furanyl)tributylstannane (production see Synthesis 1985, 898), 510 mg of lithium chloride and 693 mg of tetrakis(triphenylphosphine)palladium(O) are added to a solution of 3.50 g of 4C in 25 ml of dioxane and 0.46 ml of pyridine under protective gas. The mixture is heated to boiling for two hours, after cooling is taken up in ethyl acetate and filtered on Celite. The organic phase is dried on sodium sulfate and concentrated by evaporation in a vacuum. After column chromatography 2.79 g of 14A is obtained.

B. 11β-[4-(3-Furanyl)phenyl]-17β-hydroxy-4-estren-3-one (14B)

1.03 g of compound 14B is produced from 2.70 g of 14A analogously to instructions 4E and 7D by ketal hydrolysis and isomerization.

$^1$H-NMR(CDCl$_3$) δ: 7.74 ppm (1H,dd J=1.3 Hz and J=0.8 Hz,H-Fu2); 7.48 ppm (1H,dd J=1.8 Hz and J=1.3 Hz,HFu-5); 7.42 ppm (4H,m,H-aromatic); 6.71 ppm (1H,dd J=1.8 Hz and J=0.8 Hz,H-Fu4); 5.87 ppm (1H,s,broad,H-4); 3.60 ppm (1H,dd J=9.0 Hz and J-7.0 Hz,H-17); 3.36 ppm (1H,dd broad J=6.0 Hz and J=5.0 Hz,H-11); 2.85 ppm (1H,m,H-10); 0.57 ppm (3H,s,H-18).

C. 11β-[4-(3-furanyl)phenyl]-17β-hydroxy-17α-(3-hydroxy-1-propinyl)-4-estren-3-one (14C)

358 mg of compound 14C is produced from 1.00 g of 14B analogously to instructions 4G, 3C, 3D and 3E.

IR(KBr): 2230 cm$^{-1}$ (C≡C), 1660 cm$^{-1}$ (C=O).

D. (Z) 11β-[4-(3-furanyl)phenyl]-17β-hydroxy-17α-(3-hydroxy-1-propenyl)-4-estren-3-one (14D)

As described under 3F, 344 mg of 14C is hydrogenated with 70 mg of 10% Pd/BaSO$_4$ catalyst in 3 ml of pyridine and 6 ml of ethanol. After silica gel chromatography and crystallization from ethyl acetate/hexane 180 mg of title compound 14D is obtained.

Mp: 164°–166° C.; [α]$_D^{22}$=+99.0° (CHCl$_3$; c=0.200).
IR(KBr): 1662 cm$^{-1}$ (C=O).

Example 15

Production of (Z)-11β-[4-(2-furanyl)phenyl]-17β-hydroxy-17α(3-hydroxy-1-propenyl)-4-estren-3-one (15D)

A. 3,3-[2,2-Dimethyl-1,3-propanediylbis(oxy)]-11β-[4-(2-furanyl)phenyl]-5(10)-estren-17β-ol (15A)

1,52 g of (2-furanyl)boronic acid (production see J. Heterocyl. Chem. 1975, 195), 580 mg of lithium chloride, 8.5 ml of 2M sodium carbonate solution and 340 mg of tetrakis (triphenylphosphine)palladium(O) are added to a solution of 4.00 g of 4C in 65 ml of toluene and 25 ml of ethanol. The mixture is heated to boiling for four hours and after cooling is taken up in ethyl acetate. The organic phase is washed with 1M sodium hydroxide solution as well as with saturated sodium chloride solution, dried on sodium sulfate and concentrated by evaporation in a vacuum. After column chromatography 2.57 g of 15A is obtained.

B. 11β-[4-(2-Furanyl)phenyl]-17β-hydroxy-17α-4-estren-3-one (15B)

1.10 g of compound 15B is produced from 2.52 g of 15A analogously to instructions 4E and 7D by ketal hydrolysis and isomerization.

IR(KBr): 1664 cm$^{-1}$ (C=O).

$^1$H-NMR(CDCl$_3$+Py-d$_5$) δ: 7.60 ppm (2H,d J=9 Hz, H-aromatic); 7.47 ppm (1H, dd J=1.8 Hz and J=0.8 Hz,H-Fu5); 7.44 ppm (2H,d J=9 Hz, H-aromatic); 6.62 ppm (1H, dd J-3.5 Hz and J=1.8 Hz, H-Fu3); 6.48 ppm (1H,dd J=3.5 Hz and J=0.8 Hz, H-Fu4); 5.85 ppm (1H,s broad,H-4); 3.61 ppm (1H,dd J=9.0 Hz and J=7.0 Hz,H-17); 3.38 ppm (1H,dd broad J=5.5 Hz and J=5.0 Hz, H-11); 2.84 ppm (1H,m,H-10);0.56 ppm (3H,s,H-18).

C. 11β-[4-(2-Furanyl)phenyl]-17β-hydroxy-17α-(3-hydroxy-1-propinyl)-4-estren-3-one (15C)

313 mg of compound 15C is produced from 1.07 g of 15B analogously to instructions 4G, 3C, 3D and 3E.

IR(KBr): 2235 cm$^{-1}$ (C≡C), 1665 cm$^{-1}$ (C=O).

D. (Z)-11β-[4-(2-furanyl)phenyl]-17β-hydroxy-17α-(3-hydroxy-1-propenyl)-4-estren-3-one (15D)

As described under 3F, 299 mg of 15C is hydrogenated with 61 mg of 10% Pd/BaSO$_4$ catalyst in 3 ml of pyridine and 5 ml of ethanol. After silica gel chromatography and crystallization from ethyl acetate/hexane 205 mg of title compound 15D is obtained.

Mp: 148°–149° C.; [α]$_D^{22}$=+126.5° (CHCl$_3$; c=0.350).
IR(KBr): 1660 cm$^{-1}$ (C=O).

Example 16

Production of (Z)-4'-[17β-hydroxy-17α-(3-hydroxy-1-propenyl)-3-oxo-4-estren-11β-yl][1,1'-biphenyl]-4-carbonitrile (16D)

A. 4'-[3,3-[2,2-Dimethyl-1,3-propanediylbis(oxy)]-17β-hydroxy-5(10)-estren-11β-yl]-[1,1'-biphenyl]-4-carbonitrile (16A)

A solution of 5.00 g of 4C in 170 ml of dioxane is stirred with 1.09 g of lithium chloride for 15 minutes at room temperature under protective gas. 13 mg of hexabutylditin and 494 mg of tetrakis(triphenylphosphine)palladium(O) are added. The reaction mixture is heated to boiling for two hours. Then 15.6 g of 4-bromobenzonitrile is added and the batch is heated to boiling for another 24 hours. After cooling, it is filtered over Celite, rewashed with ethyl acetate and concentrated by evaporation in a vacuum. After column chromatography 3.16 g of 16A is obtained.

B. 4'-[17β-Hydroxy-3-oxo-4-estren-11β-yl][1,1'-biphenyl]-4-carbonitrile (16B)

1.36 g of compound 16B is produced from 3.10 g of 16A analogously to instructions 4E and 7D by ketal hydrolysis and isomerization.

IR(KBr): 2233 cm$^{-1}$ (C≡N); 1660 cm$^{-1}$ (C=O).

$^1$H-NMR(CDCl$_3$+Py-d$_5$) δ: 7.73 ppm (2H,d J=9 Hz, H-aromatic); 7.70 ppm (2H,d J=9 Hz, H-aromatic); 7.53 ppm (4H,m,H-aromatic); 5.87 ppm (1H,s,broad,H-4); 3.60 ppm (1H,dd J=9.0 Hz and J=7.5 Hz,H-17); 3.43 ppm (1H,dd broad J=6.0 Hz and J-5.0 Hz,H-11); 2.85 ppm (1H,m,H-10); 0.57 ppm (3H,s,H-18).

C. 4'-[17β-Hydroxy-17α-(3-hydroxy-1-propinyl)-3-oxo-4-estren-11β-yl][1,1'-biphenyl]-4-carbonitrile (16C)

405 mg of compound 16C is produced from 1.32 g of 16B analogously to instructions 4G, 3C, 3D and 3E.

IR(KBr): 2230 cm$^{-1}$ (C≡N and C≡C); 1658 cm$^{-1}$ (C=O).

D. (Z)-4'-[17β-Hydroxy-17-α-(3-hydroxy-1-propenyl)-3-oxo-4-estren-11β-yl][1,1'-biphenyl]-4-carbonitrile (16D)

As described under 3F 386 mg of 16C is hydrogenated with 77 mg of 10% Pd/BaSO$_4$ catalyst in 4 ml of pyridine and 6 ml of ethanol. After silica gel chromatography and crystallization from ethyl acetate/hexane 242 mg of title compound 16D is obtained.

Mp: 259°–260° C.; [α]$_D^{22}$=+135.2° (CHCl$_3$; c=0.510).
IR(KBr): 2230 cm$^{-1}$ (C≡N); 1664 cm$^{-1}$ (C=O).

Example 17

Production of 11β-(4-ethenylphenyl)-17β-hydroxy-17α-methyl-4-estren-3-one (17E)

A. 3,3-[2,2-Dimethyl-1,3-propanediylbis(oxy)]-11β-(4-ethenylphenyl)-5(10)-estren-17β-ol (17A)

2.40 ml of ethenyltributylstannane, 554 mg of lithium chloride and 378 mg of tetrakis(triphenylphosphine) palladium(O) are added to a solution of 4.00 g of 4C in 50 ml of dimethylformamide under protective gas. The mixture is heated to 110° C. in 150 minutes, after cooling it is taken up in ethyl acetate and filtered over Celite. The filtrate is washed with saturated sodium chloride solution, dried on sodium sulfate and concentrated by evaporation in a vacuum. After column chromatography 3.11 g of 17A is obtained.

B. 11β-(4-ethenylphenyl)-17β-hydroxy-4-estren-3-one (17B)

1.09 g of compound 17B is produced from 3.08 g of 17A analogously to instructions 4E and 7D by ketal hydrolysis and isomerization.

IR(KBr): 1663 cm$^{-1}$ (C=O).

C. 3,3-[1,2-Ethanediylbis(thio)]-11β-(4-ethenylphenyl)-4-estren-17-one (17C)

805 mg of compound 17C is produced from 1.06 g of 17B analogously to instructions 4G and 3C by thioketalization and oxidation.

IR(KBr): 1736 cm$^{-1}$ (C=O).

D. 3,3-[1,2-Ethanediylbis(thio)]-11β-(4-ethenylphenyl)-17α-methyl-4-estren-17β-ol (17D)

11.9 mg of a 1.6M solution of methyllithium in diethyl ether is instilled in a solution of 780 mg of 17C in 20 ml of tetrahydrofuran under protective gas. The reaction mixture is stirred for 30 more minutes and then poured into saturated ammonium chloride solution. The aqueous phase is extracted with ethyl acetate. The organic phase is washed with water, dried on sodium sulfate and concentrated by evaporation in a vacuum. After column chromatography 629 mg of 17D is obtained.

E. 11β-(4-Ethenylphenyl)-17β-hydroxy-17α-methyl-4-estren-3-one (17E)

As described under 3E 216 mg of title compound 17E is produced from 605 mg of 17D with 4.23 g of glyoxylic acid and 3.70 ml of 4M aqueous hydrochloric acid in 10 ml of acetone and 10 ml of glacial acetic acid.

$[\alpha]_D^{22}$=+151.8° (CHCl$_3$; c=0.505).

IR(KBr): 1666 cm$^{-1}$ (C=O).

$^1$H-NMR(CDCl$_3$) δ: 7.39 ppm (2H,d J=9.0 Hz, H-aromatic); 7.33 ppm (2H,d J-9.0 Hz, H-aromatic); 6.70 ppm (1H,dd J=17.0 Hz and J=10.5 Hz, H-vinyl); 5.86 ppm (1H,s,broad, H-4); 5.73 ppm (1H,d J=17.0 Hz,H-vinyl); 5.22 ppm (1H,d J=10.5 Hz,H-vinyl); 3.39 ppm (1H,dd broad J=9.5 Hz and J=4.5 Hz, H-11); 2.87 ppm (1H,m,H-10); 1.22 ppm (3H,s,H—CH$_3$); 0.66 ppm (3H, s,H-18).

Example 18

Production of (Z)-17β-hydroxy-17α-(3-hydroxy-1-propenyl)-11β-(4-methylphenyl)-4-estren-3-one (18D)

A. 3,3-[2,2-Dimethyl-1,3-propanediylbis(oxy)]-11β-(4-methylphenyl)-5(10)-estren-17β-ol (18A)

27.8 ml of a 1.6M solution of methyllithium in diethyl ether is instilled in a suspension of 2.10 g of copper(I) cyanide in 40 ml of diethyl ether and 10 ml of tetrahydrofuran at −78° C. under protective gas. The reaction solution is heated to −20° C. and, after 15 minutes, is again cooled to −78° C. At this temperature, a solution of 4.00 g of 4C in 25 ml of diethyl ether is instilled. The reaction mixture is slowly heated to −20° C. and stirred at this temperature for two days. Saturated ammonium chloride solution is added for working up and extraction with ethyl acetate is performed. The organic phase is washed with water and saturated sodium chloride solution, dried on sodium sulfate and concentrated by evaporation in a vacuum. Column chromatography yields 1.65 g of 18A.

B. 17β-Hydroxy-11β-(4-methylphenyl)-4-estren-3-one (18B)

920 mg of compound 18B is produced from 1.61 g of 18A analogously to instructions 4E and 7D by ketal hydrolysis and isomerization.

IR(KBr): 1662 cm$^{-1}$ (C=O).

C. 17β-Hydroxy-17α-(3-hydroxy-1-propinyl)-11β-(4-methylphenyl)-4-estren-3-one (18C)

294 mg of compound 18C is produced from 895 mg of 18B analogously to instructions 4G, 3C, 3D and 3E.

$[\alpha]_D^{22}$=−26.6° (c=0.500)

IR(KBr): 2230 cm$^{-1}$ (C≡C), 1659 cm$^{-1}$ (C=O).

$^1$H-NMR(CDCl$_3$) δ: 7.29 ppm (2H,d J=8.0 Hz, H-aromatic); 7.09 ppm (2H,d J=8.0 Hz, H-aromatic); 5.86 ppm (1H,s broad,H-4); 4.37 ppm (2H,m,H—CH$_2$OH); 3.39 ppm (1H,dd broad J=6.5 Hz and J=5.0, Hz,H-11); 2.85 ppm (1H,m,H-10); 2.32 ppm (3H,s, ,H—CH$_3$); 0.76 ppm (3H,s, H-18).

D. (Z) 17β-Hydroxy-17α-(3-hydroxy-1-propenyl)-11β-(4-methylphenyl)-4-estren-3-one (18D)

As described under 3F, 265 mg of 18C is hydrogenated with 53 mg of 10% Pd/BaSO$_4$ catalyst in 3 ml of pyridine and 6 ml of ethanol. After silica gel chromatography 193 mg of title compound 18D is obtained.

$[\alpha]_D^{22}$=+75.8° (CHCl$_3$; c=0.510).

IR(KBr): 1664 cm$^{-1}$ (C=O).

$^1$H-NMR(CDCl$_3$) δ: 7.29 ppm (2H,d J=8.0 Hz, H-aromatic); 7.09 ppm (2H,d J=8.0 Hz, H-aromatic); 5.85 ppm (1H,s broad, H-4);5.71 ppm (1H,ddd J=12.0 Hz and J=5.5 Hz and J=5.5 Hz, H—CH=);5.62 ppm (1H,d,broad J=12.0 Hz,H—CH=); 4.24 ppm (2H,m,H—CH$_2$OH); 3.33 ppm (1H,dd broad J=6.0 Hz and J=5.0 Hz,H-11); 2.84 ppm (1H,m,H-10); 2.32 ppm (3H,s,H—CH$_3$);0.71 ppm (3H,s,H-18).

Example 19

Production of (Z)-17β-hydroxy-17α-(3-hydroxy-1-propenyl)-11β-[4-(5-pyrimidinyl)phenyl]-4-estren-3-one (19D)

A. 3,3-[2,2-Dimethyl-1,3-propanediylbis(oxy)]-11β-[4-(5-pyrimidinyl)phenyl]-5(10)-estren-17β-ol (19A)

A solution of 4.40 g of 4C in 300 ml of dioxane is stirred with 1.35 g of lithium chloride for 15 minutes at room temperature under protective gas. 8.3 ml of hexabutylditin and 735 mg of tetrakis(triphenylphosphine)palladium(O) are added. The reaction mixture is heated to 100° C. for 90 minutes. Then 2.3 g of 5-bromopyrimidine is added and the batch is heated to boiling for another 7 hours. After cooling it is filtered over Celite, rewashed with ethyl acetate and concentrated by evaporation in a vacuum. After column chromatography 2.37 g of 19A is obtained.

B. 17β-Hydroxy-11β-11β-[4-(5-pyrimidinyl)phenyl]-4-estren-3-one (19B)

991 mg of compound 19B is produced from 2.31 g of 19A analogously to instructions 4E and 7D by ketal hydrolysis and isomerization.

IR(KBr): 1660 cm$^{-1}$ (C=O).

$^1$H-NMR(CDCl$_3$+Py-d$_5$) δ: 9.19 ppm (1H,s broad,H-Py2); 8.99 ppm (2H,s broad,H-Py4 and Py6); 7.60 ppm (2H,d J=9 Hz, H-aromatic); 7.53 ppm (2H,d J=9 Hz, H-aromatic); 5.87 ppm (1H,s broad,H-4); 3.60 ppm (1H,dd J=8.5 Hz and J=7.0 Hz, H-17); 3.43 ppm (1H,dd broad J=6.0 Hz and J=5.0 Hz,H-11); 2.84 ppm (1H,m,H-10); 0.57 ppm (3H,s,H-18).

C. 17β-Hydroxy-17α-(3-hydroxy-1-propinyl)-11β-[4-(5-pyrimidinyl)phenyl]-4-estren-3-one (19C)

203 mg of compound 19C is produced from 955 mg of 19B analogously to instructions 4G, 3C, 3D and 3E.

IR(KBr): 2235 cm$^{-1}$ (C≡C), 1665 cm$^{-1}$ (C=O).

D. (Z)-17β-Hydroxy-17α-(3-hydroxy-1-propenyl)-11β-[4-(5-pyrimidinyl)phenyl]-4-estren-3-one (19D)

As described under 3F, 187 mg of 19C is hydrogenated with 37 mg of 10% Pd/BaSO$_4$ catalyst in 2 ml of pyridine and 4 ml of ethanol. After silica gel chromatography 112 mg of title compound 19D is obtained.

IR(KBr): 1664 cm$^{-1}$ (C=O).
$^1$H-NMR(CDCl$_3$) δ: 9.20 ppm (1H,s broad,H-Py2); 8.98 ppm (2H,s broad,H-Py4 and Py6); 7.59 ppm (2H, d J=9 Hz, H-aromatic); 7.52 ppm (2H,d J=9 Hz, H-aromatic); 5.88 ppm (1H,s broad,H-4); 5.72 ppm (1H,ddd,J=11.5 Hz and J=5.5 Hz and J-5.5 Hz,H—CH=); 5.65 ppm (1H,d broad J=11.5 Hz,H—CH=); 4.29 ppm (1H,dd broad J=14 Hz and J=5.5 Hz,H—CH$_2$OH); 4.26 ppm (1H,dd broad J=14 Hz and J=5.5 Hz,H—CH$_2$OH); 3.44 ppm (1H,dd broad J=6.0 Hz and J=5.0 Hz,H-11); 2.85 ppm (1H,m,H-10); 0.72 ppm (3H,s,H-18).

Example 20

Preparation of (11β,17β)-11-[4-(5-pyrimidinyl)phenyl]spiro[estr-4-en-17,2'(3'H)-furan]-30-one (20A)

A. (11β,17β)-11-[4-(5-pyrimidinyl)phenyl]-spiro[estr-4-en-17,2'(3'H)-furan]-30-one (20A)

320 mg of the compound described under 19D were brought together at 0° C. with 400 mg of toluene sulfonic acid chloride and 1 ml of triethylamine. The reaction mixture was stirred for 12 hours at room temperature and then mixed with a saturated solution of sodium hydrogen carbonate and was extracted with methylene chloride. The organic phase was washed with a saturated sodium chloride solution, dried over sodium sulfate and exhausted under a vacuum. Chromatography produces 140 mg of 20A.

$^1$H-NMR(CDCl$_3$) δ: 9.20 ppm (1H,s broad, H-Py2); 8.98 ppm (2H,s broad, H-Py4 and Py6); 7.57 ppm (2H,d J=9 Hz,H-aromatic); 7.52 ppm (2H,d J=9 Hz,H-aromatic); 5.88 ppm (1H,s broad,H-4); 5.86 (1H,m,H—CH=); 5.81 ppm (1H,m,H—CH=); 4.52 ppm (1H,d broad J=14 Hz,H—CH$_2$OC); 4.49 ppm (1H,d broad J=14 Hz,H—CH$_2$OC); 3.39 ppm (1H,dd broad J=9.0 Hz and J=4.0 Hz,H-11); 2.84 ppm (1H,m,H-10); 0.71 ppm (3H,s,H-18).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A method of inducing an antigestagenic effect, comprising administering an antigestagenically effective amount of an 11β-aryl-4-estrene of formula I having progesterone antagonist activity wherein
X is an oxygen atom, the hydroxyimino grouping >N—OH or two hydrogen atoms $R^1$ is hydrogen or a methyl group, $R^2$ is a hydroxy group, a $C_1$–$C_{10}$ alkoxy or $C_1$–$C_{10}$ alkanoyloxy group, $R^3$ is hydrogen, 1-propinyl, 2-propenyl, the grouping —(CH$_2$)$_n$CH$_2$Z, wherein
n is 0, 1, 2, 3, 4 or 5,
Z is hydrogen, cyano or the radical —OR$^5$, wherein R$^5$ is H $C_1$–$C_{10}$ alkyl or $C_1$–$C_{10}$ alkanoyl,
the grouping —(CH$_2$)$_m$C≡C—Y, wherein
m is 0, 1 or 2 and
Y is hydrogen, fluorine, chlorine, bromine or iodine atom; or a $C_1$–$C_{10}$ hydroxyalkyl, $C_1$–$C_{10}$ alkoxyalkyl, or $C_1$–$C_{10}$ alkanoyloxyalkyl radical,
the grouping —(CH$_2$)$_p$—CH=CH—(CH$_2$)$_k$CH$_2$R$^6$, wherein
p is 0 or 1,
k is 0, 1 or 2, and
R$^6$ means a hydrogen atom, a hydroxy group, a $C_1$–$C_4$ alkoxy or $C_1$–$C_4$ alkanoyloxy radical, or else R$^2$ and R$^3$ together stand for a radical of the formula wherein x=1 or 2, $R^4$ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group in which R$^7$ and R$^8$, each independently of one another, is hydrogen or a $C_1$–$C_4$ alkyl group; a corresponding amine oxide a grouping —OR$^9$ or —S(O)$_i$R$^9$, wherein
i is 0, 1 or 2,
R$^9$ means hydrogen, a methyl, ethyl, propyl, isopropyl, methoxyphenyl, allyl or a 2-dimethylaminoethyl group;

a heteroaryl radical for the formula Iα wherein
A is a nitrogen oxygen or sulfur atom, —B—D—E— is the element sequence —C—C—C—, —N—C—C— or —C—N—C—, and R$^{10}$ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group

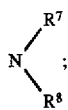

or the radical —$OR^9$ or —$S(O)_iR^9$, wherein $R^7$, $R^8$, $R^9$ and i each independently has one of the meanings already indicated;

a heteroaryl radical of formula Iβ

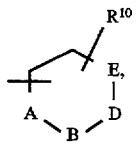 (Iβ)

wherein

A is a nitrogen atom,
—B—D—E— is the element sequence —C—C—C—, —N—C—C—, —C—N—C— or —C—C—N—, and
$R^{10}$ has the meaning already indicated; or a phenyl radical of formula Iτ

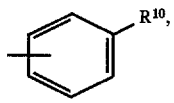 (Iτ)

wherein $R^{10}$ has the meaning already indicated,
or a pharmacologically compatible addition salt thereof.

2. A method of inducing abortion, comprising administering an effective amount of an 11β-aryl-4-estrene of formula I having progesterone antagonist activity

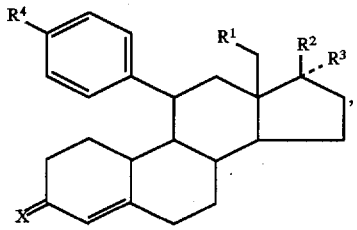 (I)

wherein

X is an oxygen atom, the hydroxyimino grouping >N—OH or two hydrogen atoms $R^1$ is hydrogen or a methyl group, $R^2$ is a hydroxy group, a $C_1$–$C_{10}$ alkoxy or $C_1$–$C_{10}$ alkanoyloxy group, $R^3$ is hydrogen, 1-propinyl, 2-propenyl, the grouping —$(CH_2)_nCH_2Z$, wherein
  n is 0, 1, 2, 3, 4 or 5,
  Z is hydrogen, cyano or the radical —$OR^5$, wherein $R^5$ is H, $C_1$–$C_{10}$ alkyl or $C_1$–$C_{10}$ alkanoyl,
the grouping —$(CH_2)_mC\equiv C$—Y, wherein
  m is 0, 1 or 2 and
  Y is hydrogen, fluorine, chlorine, bromine or iodine atom; or a $C_1$–$C_{10}$ hydroxyalkyl, $C_1$–$C_{10}$ alkoxyalkyl, or $C_1$–$C_{10}$ alkanoyloxyalkyl radical,
the grouping —$(CH_2)_p$—CH=CH—$(CH_2)_kCH_2R^6$, wherein
  p is 0 or 1,
  k is 0, 1 or 2, and
  $R^6$ means a hydrogen atom, a hydroxy group, a $C_1$–$C_4$ alkoxy or $C_1$–$C_4$ alkanoyloxy radical, or else $R^2$ and $R^3$ together stand for a radical of the formula

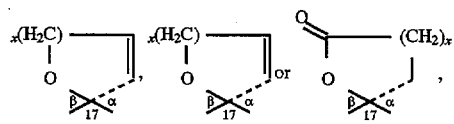

wherein x=1 or 2, $R^4$ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group

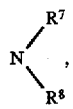

in which $R^7$ and $R^8$, each independently of one another is hydrogen or a $C_1$–$C_4$ alkyl group; a corresponding amine oxide

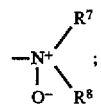

a grouping —$OR^9$ or —$S(O)_iR_9$, wherein
  is 0, 1 or 2,
  $R^9$ means hydrogen, a methyl, ethyl, propyl, isopropyl, methoxyphenyl, allyl or a 2-dimethylaminoethyl group;

a heteroaryl radical for the formula Iα

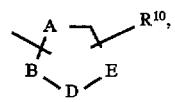 (Iα)

wherein

A is a nitrogen, oxygen or sulfur atom —B—D—E— is the element sequence —C—C—, —N—C—C— or —C—N—C—, and $R^{10}$ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group

or the radical —$OR^9$ or —$S(O)_iR^9$, wherein

R⁷, R⁸, R⁹ and i each independently has one of the meanings already indicated;

a heteroaryl radical of formula Iβ

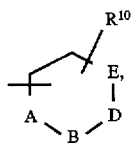 (Iβ)

wherein

A is a nitrogen atom —B—D—E— is the element sequence —C—C—C—, —N—C—C—, —C—N—C— or —C—C—N—, and R¹⁰ has the meaning already indicated; or a phenyl radical of formula Iτ

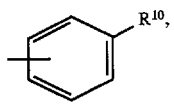 (Iτ)

wherein R¹⁰ has the meaning already indicated, or a pharmacologically compatible addition salt thereof.

3. A method of post-coital birth control, comprising administering an effective amount of an 11β-aryl-4-estrene of formula I having progesterone antagonist activity

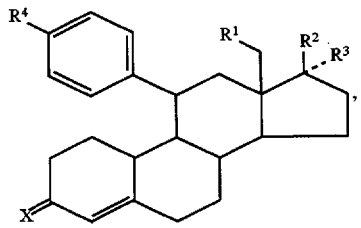 (I)

wherein

X is an oxygen atom, the hydroxyimino grouping >N—OH or two hydrogen atoms,

R¹ is hydrogen or a methyl group,

R² is a hydroxy group, a $C_1$–$C_{10}$ alkoxy or $C_1$–$C_{10}$ alkanoyloxy group, R³ is hydrogen, 1-propinyl, 2-propenyl, the grouping —(CH₂)ₙCH₂Z, wherein n is 0, 1, 2, 3, 4 or 5, Z is hydrogen, cyano or the radical —OR⁵, wherein R⁵ is H, $C_1$–$C_{10}$ alkyl or $C_1$–$C_{10}$ alkanoyl, the grouping —(CH₂)ₘC≡C—Y, wherein m is 0, 1 or 2 and Y is hydrogen, fluorine, chlorine, bromine or iodine atom; or a $C_1$–$C_{10}$ hydroxyalkyl, $C_1$–$C_{10}$ alkoxyalkyl, or $C_1$–$C_{10}$ alkanoyloxyalkyl radical, the grouping —(CH₂)ₚ—CH=CH—(CH₂)ₖCH₂R⁶, wherein p is 0 or 1, k is 0, 1 or 2, and R⁶ means a hydrogen atom, a hydroxy group, a $C_1$–$C_4$ alkoxy or $C_1$–$C_4$ alkanoyloxy radical, or else R² and R³ together stand for a radical of the formula

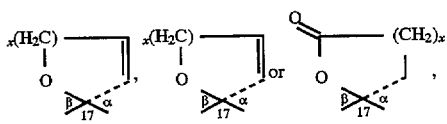

wherein x=1 or 2,

R⁴ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group

in which R⁷ and R⁸, each independently of one another, is hydrogen or a $C_1$–$C_4$ alkyl group; a corresponding amine oxide

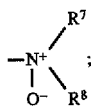

a grouping —OR⁹ or —S(O)ᵢR⁹, wherein i is 0, 1 or 2,

R⁹ means hydrogen, a methyl, ethyl, propyl, isopropyl, methoxyphenyl, allyl or a 2-dimethylaminoethyl group;

a heteroaryl radical for the formula Iα

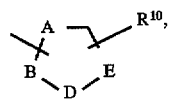 (Iα)

wherein

A is a nitrogen, oxygen or sulfur atom, —B—D—E— is the element sequence —C—C—C—, —N—C—C— or —C—N—C—, and R¹⁰ is hydrogen; cyano; chlorine; fluorine; bromine; iodine; trialkylsilyl; trialkylstannyl; a straight-chain or branched, saturated or unsaturated $C_{1-8}$ hydrocarbyl, $C_{1-8}$ alkanoyl or $C_{1-8}$ alkoxyalkyl radical; an amino group

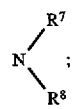

or the radical —OR⁹ or —S(O)ᵢR⁹, wherein

R⁷, R⁸, R⁹ and i each independently has one of the meanings already indicated;

a heteroaryl radical of formula Iβ

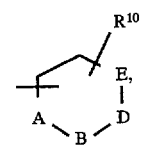 (Iβ)

wherein

A is a nitrogen atom, —B—D—E— is the element sequence —C—C—C—, —N—C—C—, —C—N—C— or —C—C—N—, and R$^{10}$ has the meaning already indicated;

or a phenyl radical of formula Iτ

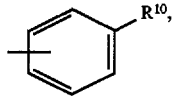 (Iτ)

wherein R$^{10}$ has the meaning already indicated, or a pharmacologically compatible addition salt thereof.

4. A method of treating endometriosis, comprising administering an effecting amount of an 11β-aryl-4-estrene of formula I having progesterone antagonist activity

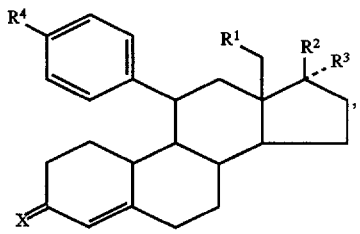 (I)

wherein

X is an oxygen atom, the hydroxyimino grouping >N—OH or two hydrogen atoms,

R$^1$ is hydrogen or a methyl group,

R$^2$ is a hydroxy group, a C$_1$-C$_{10}$ alkanoyloxy group,

R$^3$ is hydrogen, 1-propinyl, 2-propenyl, the grouping —(CH$_2$)$_n$CH$_2$Z, wherein n is 0, 1, 2, 3, 4 or 5, Z is hydrogen, cyano or the radical —OR$^5$, wherein R$^5$ is H, C$_1$-C$_{10}$ alkyl or C$_1$-C$_{10}$ alkanoyl, the grouping —(CH$_2$)$_m$C≡C—Y, wherein m is 0, 1 or 2 and Y is hydrogen, fluorine, chlorine, bromine or iodine atom; or a C$_1$-C$_{10}$ hydroxyalkyl, C$_1$-C$_{10}$ alkoxyalkyl, or C$_1$-C$_{10}$ alkanoyloxyalkyl radical, the grouping —(CH$_2$)$_p$—CH═CH—(CH$_2$)$_k$CH$_2$R$^6$, wherein p is 0 or 1, k is 0, 1 or 2, and R$^6$ means a hydrogen atom, a hydroxy group, a C$_1$-C$_4$ alkoxy or C$_1$-C$_4$ alkanoyloxy radial, or else R$^2$ and R$^3$ together stand for a radical of the formula

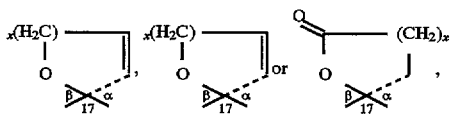

wherein x=1 or 2

R$^4$ is hydrogen; cyano; chlorine; fluorine; bromine; iodine; trialkylsilyl; trialkylstannyl; a straight-chain or branched, saturated or unsaturated C$_{1-8}$ hydrocarbyl, C$_{1-8}$ alkanoyl or C$_{1-8}$ alkoxyalkyl radical; an amino group

in which R$^7$ and R$^8$, each independently of one another, is hydrogen or a C$_1$-C$_4$ alkyl group; a corresponding amine oxide

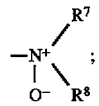

a grouping —OR$^9$ or —S(O)$_i$R$^9$, wherein i is 0, 1 or 2,

R$^9$ means hydrogen, a methyl, ethyl, propyl, isopropyl, methoxyphenyl, allyl or a 2-dimethylaminoethyl group;

a heteroaryl radical for the formula Iα

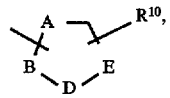 (Iα)

wherein

A is a nitrogen, oxygen or sulfur atom, —B—D—E— is the element sequence —C—C—C—, —N—C—C— or —C—N—C—, and R$^{10}$ is hydrogen; cyano; chlorine; fluorine; bromine; iodine; trialkylsilyl; trialkylstannyl; a straight-chain or branched, saturated or unsaturated C$_{1-8}$ hydrocarbyl, C$_{1-8}$ alkanoyl or C$_{1-8}$ alkoxyalkyl radical; an amino group

or the radical —OR$^9$ or —S(O)$_i$R$^9$, wherein

R$^7$, R$^8$, R$^9$ and i each independently has one of the meanings already indicated;

a heteroaryl radical of formula Iβ

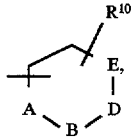 (Iβ)

wherein

A is a nitrogen atom, —B—D—E— is the element sequence —C—C—C—, —N—C—C—, —C—N—C— or —C—C—N—, and R$^{10}$ has the meaning already indicated;

or a phenyl radical of formula Iτ

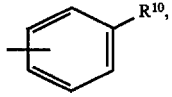 (Iτ)

whereto R$^{10}$ has the meaning already indicated, or a pharmacologically compatible addition salt thereof.

5. A method of claim 1, wherein X is an oxygen atom.

6. A method of claim 1, wherein the 11β-aryl group is 4-acetylphenyl.

7. A method of claim 1, wherein the 11β-aryl group is 4-dimethylaminophenyl.

8. A method of claim 1, wherein the 11β-aryl group is 4-(3-furyl)phenyl.

9. A method of claim 1, wherein the 11β-aryl group is 4-(3-pyridinyl)phenyl.

10. A method of claim 1, wherein the 11β-aryl group is 4-ethylphenyl.

11. A method of claim 1, wherein the 11β-aryl group is 4-(3-pyridyl)phenyl.

12. A method of claim 1, wherein the 11β-aryl group is 4-(5-pyrimidinyl)phenyl.

13. A method of claim 1, wherein the 11β-aryl group is 4-(4-cyanophenyl)phenyl.

14. A method of claim 1, wherein the 11β-aryl group is 4-vinylphenyl.

15. A method of claim 1, wherein the 11β-aryl group is 4-(1-hydroxyethyl)phenyl.

16. A method of claim 1, wherein the compound is:

11β-[4-(dimethylamino)phenyl]-17β-hydroxy-17α-(1-propinyl)-4-estren-3-one;
11β-(4-acetylphenyl)-17β-hydroxy-4-estren-3-one;
11β-(4-acetylphenyl)-17β-hydroxy-17α(1-propinyl)-4-estren-3-one;
11β-(4-acetylphenyl)-17β-hydroxy-17α-(3-hydroxy-1Z-propenyl)-4-estren-3-one;
11β-[4-(dimethylamino)phenyl]-17β-hydroxy-17α-(3-hydroxy-1Z-propenyl)-4-estren-3-one;
11β-[4-(3-furyl)phenyl]-17β-hydroxy-17α-(1-propinyl)-4-estren-3-one;
11β-[4-(3-furyl)phenyl]-17β-hydroxy-17α-(3-hydroxy-1Z-propenyl)-4-estren-3-one;
11β-[4-(5-pyrimidinyl)phenyl]-17β-hydroxy-17α-(1-propinyl)-4-estren-3-one;
11β-[4-(5-pyrimidinyl)phenyl]-17β-hydroxy-17α-(3-hydroxy-1Z-propenyl)-4-estrene-3-one;
11β-[4-(3-pyridyl)phenyl]-17β-hydroxy-17α-(1-propinyl)-4-estren-3-one;
11β-[4-(3-pyridyl)phenyl]-17β-hydroxy-17α-(3-hydroxy-1Z-propenyl)-4-estrene-3-one;
11β-[4-(4-cyanophenyl)phenyl]-17β-hydroxy-17α-(1-propinyl)-4-estren-3-one;
11β-[4-(4-cyanophenyl)phenyl]-17β-hydroxy-17α-(3-hydroxy-1Z-propenyl)-4-estren-3-one;
11β-(4-vinylphenyl)-17β-hydroxy-17α-(3-hydroxy-1Z-propenyl)-4-estren-3-one;
11β-(4-vinylphenyl)-17β-hydroxy-17α-(1-propinyl)-4-estren-3-one;
11β-[4-(1-hydroxyethyl)phenyl]-17β-hydroxy-17α-(3-hydroxy-1Z-propenyl)-4-estren-3-one;
11β-[4-(1-hydroxyethyl)phenyl]-17β-hydroxy-17α-(1-propinyl)-4-estren-3-one;
11β-[4-(dimethylamino)phenyl]-17β-hydroxy-17α-methoxymethyl-4-estren-3-one;
11β-[4-(dimethylamino)phenyl]-17β-hydroxy-17α-cyanomethyl-4-estren-3-one;
(11β,17β)-4',5'-dihydro-11-[4-(dimethylamino)phenyl]-spiro[estr-4-ene-17,2'(3'H)-furan]-3-one;
(11β,17β)-3',4'-dihydro-11-[4-(dimethylamino)phenyl]-spiro[estr-4-ene-17,2'(5'H)-furan]-3,5'-dione;
(11β,17β)-11-[4-(dimethylamino)phenyl]spiro[estr-4-ene-17,2'(5'H)-furan]-3-one;
11β-[4-(dimethylamino)phenyl]-17α-(1-propinyl)-4-estren-17β-ol;
17β-hydroxy-3-oxo-11β-[4-(3-pyridinyl)phenyl]-4-estren-17α-acetonitrile;
(E)-17β-hydroxy-3-(hydroxyimino)-11β-[4-(3-pyridinyl)phenyl]-4-estren-17α-acetonitrile;
(Z)-17β-hydroxy-3-(hydroxyimino)-11β-[4-(3-pyridinyl)phenyl]-4-estren-17α-acetonitrile;
17β-hydroxy-17α-(2-propenyl)-11β-[4-(3-pyridinyl)phenyl]-4-estren-3-one;
17β-hydroxy-17α-(methoxymethyl)-11β-[4-(3-pyridinyl)phenyl]-4-estren-3-one;
11β-(4-ethylphenyl)-17β-hydroxy-17α-(1-propinyl)-4-estren-3-one;
(Z)-11β-(4-ethylphenyl)-17β-hydroxy-17α-(3-hydroxy-1-propenyl)-4-estren-3-one;
(Z)-11β-[4-(2-furanyl)phenyl]-17β-hydroxy-17α-(3-hydroxyl-1-propenyl)4-estren-3-one;
11β-(4-ethylphenyl)-17β-hydroxy-17α-methyl)-4-estren-3-one;
(Z)-17β-hydroxy-17α-(3-hydroxy-1-propenyl)-11β-(4-methylphenyl)-4-estren-3-one; or
(11β,17β)-11-[4-(5-pyrimidinyl)phenyl]spiro[estr-4-en-17,2'(3'H)-furan]-3-one.

17. A method of claim 1, wherein $R^3$ is 2-propenyl.

18. A method of claim 1, wherein $R^3$ is 3-hydroxy-1Z-propenyl.

19. A method of claim 1, wherein $R^3$ is 1-propinyl.

20. A method of claim 1, wherein the compound is 11β-[4-(dimethylamino)phenyl]-17β-hydroxy-17α-(3-hydroxy-1Z-propenyl)-4-estren-3-one.

21. A method of claim 3, wherein the 11β-aryl group is 4-(3-furyl)phenyl.

22. A method of claim 3, wherein the 11β-aryl group is 4-(3-pyridinyl)phenyl.

23. A method of claim 3, wherein the 11β-aryl group is 4-(3-pyridyl)phenyl.

24. A method of claim 3, wherein the 11β-aryl group is 4-(5-pyrimidin-yl)phenyl.

25. A method of claim 3, wherein the 11β-aryl group is 4-vinylphenyl.

26. A method of claim 3, wherein the 11β-aryl group is 4-(1-hydroxyethyl)phenyl.

* * * * *